(12) United States Patent
Doudna et al.

(10) Patent No.: US 10,570,418 B2
(45) Date of Patent: Feb. 25, 2020

(54) METHODS AND COMPOSITIONS FOR RNA-DIRECTED TARGET DNA MODIFICATION

(71) Applicant: The Regents of the University of California, Oakland, CA (US)

(72) Inventors: Jennifer A. Doudna, Berkeley, CA (US); Steven Lin, Albany, CA (US); Brett T. Staahl, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/502,720

(22) PCT Filed: Sep. 1, 2015

(86) PCT No.: PCT/US2015/047966
§ 371 (c)(1),
(2) Date: Feb. 8, 2017

(87) PCT Pub. No.: WO2016/036754
PCT Pub. Date: Mar. 10, 2016

(65) Prior Publication Data
US 2018/0044700 A1    Feb. 15, 2018

Related U.S. Application Data

(60) Provisional application No. 62/044,812, filed on Sep. 2, 2014.

(51) Int. Cl.
| | | |
|---|---|---|
| *C12N 15/63* | (2006.01) | |
| *C12N 15/87* | (2006.01) | |
| *C07H 21/02* | (2006.01) | |
| *C07H 21/04* | (2006.01) | |
| *C07K 14/00* | (2006.01) | |
| *A61K 31/16* | (2006.01) | |
| *C12N 15/90* | (2006.01) | |
| *C07K 14/315* | (2006.01) | |
| *A61K 31/165* | (2006.01) | |
| *A61K 48/00* | (2006.01) | |

(52) U.S. Cl.
CPC .......... *C12N 15/907* (2013.01); *A61K 31/165* (2013.01); *A61K 48/00* (2013.01); *C07H 21/02* (2013.01); *C07H 21/04* (2013.01); *C07K 14/315* (2013.01); *C12N 15/63* (2013.01); *C12N 2310/20* (2017.05)

(58) Field of Classification Search
CPC .. C12N 15/63; C12N 15/907; C12N 2310/20; C07H 21/02; C07H 21/04; C07K 14/315; A61K 31/165

USPC ....... 435/455, 463; 536/23.1, 23.7; 530/350; 514/629
See application file for complete search history.

(56) References Cited

U.S. PATENT DOCUMENTS

| | | |
|---|---|---|
| 8,696,359 B2 | 4/2014 | Clark et al. |
| 2005/0207633 A1 | 9/2005 | Arini et al. |
| 2005/0273870 A1 | 12/2005 | Robl et al. |
| 2014/0227787 A1 | 8/2014 | Zhang |
| 2014/0242699 A1 | 8/2014 | Zhang |

FOREIGN PATENT DOCUMENTS

| | | |
|---|---|---|
| WO | WO 2001/019182 | 3/2001 |
| WO | WO 2005/108622 A2 * | 11/2005 |
| WO | WO 2013/176772 | 11/2013 |

OTHER PUBLICATIONS

Kotterman et al., 2014, Nature Reviews, vol. 15, p. 445-451.*
Kaur et al., 2009, Current Gene Therapy, vol. 9. p. 434-458.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Glucksmann et al., 2015, US 20150232881 A1, effective filing date, Nov. 7, 2013.*
Krouse et al., 2012, US 20120088807 A1.*
Heyer, et al.; "Regulation of Homologous Recombination in Eukaryotes"; Annu. Rev. Genet.; vol. 44, pp. 113-139 (2010).
Lin, et al.; "Enhanced homology-directed human genome engineering by conrolled timing of CRISPR/Cas9 delivery"; eLife; 13 pages (Dec. 15, 2014).
Orthwein, et al.; "Mitosis Inhibits DNA Double-Strand Break Repair to Guard Against Telomere Fusions"; Science; vol. 344, No. 6180 pp. 189-193 (Mar. 20, 2014).
Shrivastav, et al.; "Regulation of DNA double-strand break repair pathway choice"; Cell Research; vol. 18, pp. 134-147 (2008).
Lundin, et al.; "Different Roles for Nonhomologous End Joining and Homologous Recombination following Replication Arrest in Mammalian Cells"; Molecular and Cellular Biology; vol. 22, No. 16, pp. 5869-5878 (Aug. 2002).

* cited by examiner

*Primary Examiner* — Shin Lin Chen
(74) *Attorney, Agent, or Firm* — Bozicevic Field & Francis, LLP; Paula A. Borden

(57) ABSTRACT

The present disclosure provides compositions and methods of site-specific modification of a target DNA, or a protein associated with a target DNA, in a eukaryotic cell. The present disclosure provides methods of binding a target DNA in a eukaryotic cell.

10 Claims, 14 Drawing Sheets
Specification includes a Sequence Listing.

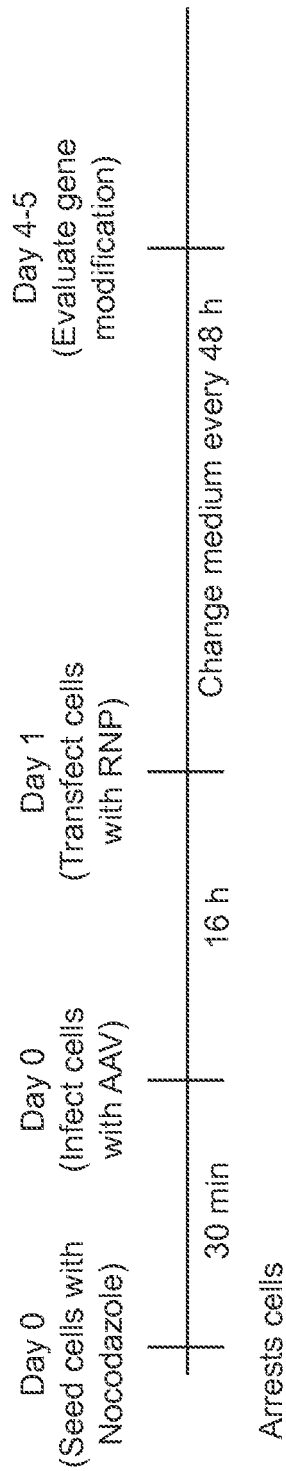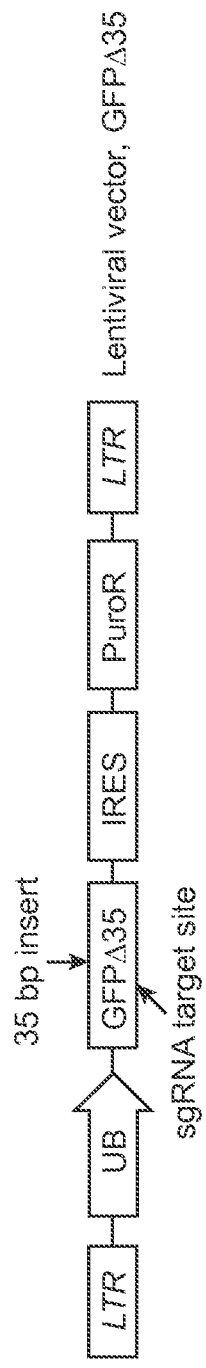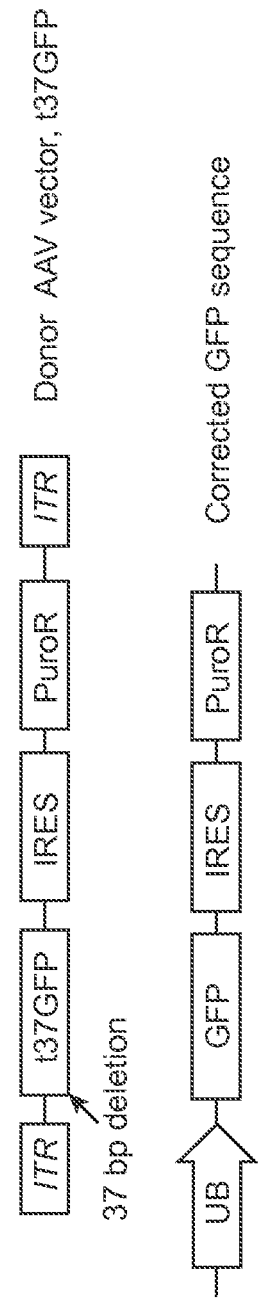
FIG. 6A
FIG. 6B

METHODS AND COMPOSITIONS FOR RNA-DIRECTED TARGET DNA MODIFICATION

CROSS-REFERENCE

This application is a national stage filing under 35 U.S.C. § 371 of PCT Patent Application No. PCT/US2015/047966, filed Sep. 1, 2015, which application claims the benefit of U.S. Provisional Patent Application No. 62/044,812, filed Sep. 2, 2014, which applications are incorporated herein by reference in their entirety.

INCORPORATION BY REFERENCE OF SEQUENCE LISTING PROVIDED AS A TEXT FILE

A Sequence Listing is provided herewith as a text file, "BERK-251WO-SeqList_ST25.txt" created on Aug. 28, 2015 and having a size of 7679 KB. The contents of the text file are incorporated by reference herein in their entirety.

INTRODUCTION

Methods for introducing site-specific double-strand DNA (dsDNA) breaks (DSBs) in genomic DNA have transformed the ability to engineer eukaryotic organisms by initiating DNA repair pathways that lead to targeted genetic reprogramming. Zinc-finger nucleases (ZFNs) and transcription activator-like effector nucleases (TALENs) have proved effective for such genomic manipulation but their use has been limited by the need to engineer a specific protein for each dsDNA target site and by off-target activity.

Research into genome defense mechanisms in bacteria showed that CRISPR (Clustered Regularly Interspaced Short Palindromic Repeats)/Cas (CRISPR-associated) loci encode RNA-guided adaptive immune systems that can destroy foreign DNA. The Type II CRISPR/Cas systems require a single protein, Cas9, to catalyze DNA cleavage. Cas9 generates blunt DSBs at sites defined by a guide sequence contained within an associated CRISPR RNA (crRNA) transcript.

Using a guide RNA, Cas9 can modify (e.g., cleave) double-stranded DNA at any site: (i) defined by the guide RNA sequence, and (ii) including a protospacer-adjacent (PAM) motif. A Cas9/guide RNA complex (i.e., a Cas9 targeting complex) constitutes a simple and versatile RNA-directed system for modifying target DNA, or modifying proteins associated with target DNA, in any desired cell or organism (e.g., in eukaryotic cells). Additionally, a Cas9 targeting complex having a mutated Cas9 protein with reduced or removed nuclease activity can still bind to target DNA.

There is a need in the art for methods that increase the efficiency of target DNA modification by Cas9 targeting complexes and/or increase the effectiveness of methods that capitalize on target DNA binding by Cas9 targeting complexes.

SUMMARY

The present disclosure provides methods and compositions for site-specific modification of a target DNA, or a protein associated with a target DNA, in a eukaryotic cell. The present disclosure provides methods of binding a target DNA in a eukaryotic cell.

Subject methods of site-specific modification and/or subject methods of binding can include a step of enriching a cell population for cells that are in a desired phase(s) of the cell cycle (e.g., the S-phase, the M-phase, the G0 phase, the G1 phase, the G2 phase, G1/S, G2/M, etc.); and a step of contacting the target DNA of cells of the enriched population of cells (e.g., in some cases the target DNA in cells of the enriched population of cells) with a Cas9 targeting complex (e.g., via introducing into the target eukaryotic cell(s) at least one component of a Cas9 targeting complex). For example, the subject methods include contacting the target DNA in the target cell(s) with: (i) a Cas9 protein; and (ii) a guide RNA comprising: a targeting sequence that hybridizes to a target sequence of the target DNA, and a protein-binding segment that interacts with the Cas9 protein. A step of enriching can include, for example, a cell separation method (e.g., mitotic shake-off, countercurrent centrifugal elutriation (CCE), flow cytometry, and the like) and/or a cell synchronization method (e.g., contact with a cell cycle blocking composition; mitogen and/or growth factor withdrawal; density arrest; and the like).

In some embodiments, a subject method of site-specific modification and/or a subject method of binding includes a step of blocking a target cell at a desired phase in the cell cycle (e.g., the S-phase, the M-phase, the G0 phase, the G1 phase, the G2 phase, G1/S, G2/M, etc.); and a step of contacting the target DNA with a Cas9 targeting complex (e.g., via introducing into the target eukaryotic cell(s) at least one component of a Cas9 targeting complex). In some cases, blocking a cell at a phase in the cell cycle includes contacting the cell with a cell cycle blocking agent.

In some cases, the above methods include a step of contacting a eukaryotic cell, or contacting a population of eukaryotic cells, with a cell cycle blocking composition. In some cases, a cell cycle blocking composition for use in the above methods includes at least one agent selected from: nocodazole, hydroxyurea; colchicine; demecolcine (colcemid); lovastatin; mimosine; thymidine; aphidicolin; latrunculin A; and latrunculin. B. The above methods include contacting the target DNA with a Cas9 targeting complex, which in some cases includes introducing into the cell (i.e., the target cell having the target DNA) at least one of: (a) a single guide RNA, (b) a DNA polynucleotide encoding a single guide RNA, (c) a targeter-RNA, (d) a DNA polynucleotide encoding a targeter-RNA, (e) an activator-RNA, (f) a DNA polynucleotide encoding an activator-RNA, (g) a Cas9 protein, and (h) a nucleic acid encoding a Cas9 protein.

In some cases, the Cas9 protein has nuclease activity and the site-specific modification is cleavage of the target DNA. In some cases, the target DNA is double stranded and the Cas9 protein: (a) cleaves the complementary strand of the target DNA, but does not cleave the non-complementary strand of the target DNA; (b) cleaves the non-complementary strand of the target DNA, but does not cleave the complementary strand of the target DNA; (c) cleaves both the complementary and non-complementary strands of the target DNA. In some cases, the above methods include contacting the target DNA with a donor polynucleotide.

In some cases, the method is a method of binding a target DNA and the Cas9 protein does not cleave the target DNA.

In some cases, the method is a method of site-specific modification of a target DNA and the Cas9 protein has a heterologous polypeptide sequence that provides for a DNA modifying activity (e.g., methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, and/or glycosylase activity.) In some cases, the method is a method of site-specific modification of a protein associated with a target DNA, and the Cas9 protein has a heterologous polypeptide sequence that provides for a protein modifying activity (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and/or demyristoylation activity).

In some embodiments, the method is a method of binding target DNA in a eukaryotic cell, and the method includes: (a) blocking the cell at a desired phase in the cell cycle; and (b) contacting the target DNA in the cell with: (i) a Cas9 protein, wherein the Cas9 protein does not cleave the target DNA, and (ii) a guide RNA comprising: a targeting sequence that hybridizes to a target sequence of the target DNA, and a protein-binding domain that interacts with the Cas9 protein. In some such cases, the Cas9 protein includes a fusion partner having at least one of: a subcellular localization sequence (e.g., a nuclear localization signal), and a detectable label (e.g., a fluorescent tag, an affinity tag, and the like).

In some embodiments, the method is a method of binding target DNA in cells of a population of eukaryotic cells, and the method includes: (a) enriching the population of eukaryotic cells for cells in a desired phase of the cell cycle; and (b) contacting the target DNA of cells of the enriched population of cells (e.g., in some cases the target DNA in cells of the enriched population of cells) with: (i) a Cas9 protein, wherein the Cas9 protein does not cleave the target DNA, and (ii) a guide RNA comprising: a targeting sequence that hybridizes to a target sequence of the target DNA, and a protein-binding domain that interacts with the Cas9 protein. In some such cases, the Cas9 protein includes a fusion partner having at least one of: a subcellular localization sequence (e.g., a nuclear localization signal), and a detectable label (e.g., a fluorescent tag, an affinity tag, and the like). In some such cases, the Cas9 protein includes a fusion partner having at least one of: a subcellular localization sequence (e.g., a nuclear localization signal), and a detectable label (e.g., a fluorescent tag, an affinity tag, and the like).

In some cases, any of the above methods are carried out in a living cell in vitro, in a living cell ex vivo, or in a living cell in vivo. In some cases, the target cell (or the population of target cells) in any of the above methods is a eukaryotic single-cell organism, a somatic cell, a germ cell, a stem cell, a plant cell, an algal cell, an animal cell, in invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, or a human cell.

Kits and compositions for carrying out the methods are also provided. In some cases, a subject kit includes a cell cycle blocking agent and at least one component of a Cas9 targeting complex (or a nucleic acid encoding at least one component of a Cas9 targeting complex).

BRIEF DESCRIPTION OF THE DRAWINGS

FIG. 3A depicts nucleotide sequences of a double stranded target (GCCAATGGGGAGGACATCGATGTCACCTCCAAT-GACTAGGGTGGGCAAC (SEQ ID NO:1408; and its complement GTTGCCCACCCTAGTCATTGGAGGT-GACATCGATGTCCTCCCCATTGGC (SEQ ID NO:1409), and various HDR templates (template 1: CCAC-CGCTACGAAGCTTGTCATTGGAGGTGACATCGAT-GTCCTC (SEQ ID NO:1410); template 2: GGATC-CAAGCTT (SEQ ID NO:1411); template 3: GGATCCAAGCTT (SEQ ID NO:1412); template 4: GGATCCAAGCTT (SEQ ID NO:1413); template 5: AAGCTTGGATCC (SEQ ID NO:1414); template 6: AAGCTTGGATCC (SEQ ID NO:1415) and its complement GGATCCAAGCTT (SEQ ID NO:1416); template 7: AAGCTTGGATCC (SEQ ID NO:1417) and its complement GGATCCAAGCTT (SEQ ID NO:1418).

FIG. 6A-6F provide data related to enhanced gene targeting by cell synchronization and co-delivery of AAV and Cas9 ribonucleoprotein (RNP). FIG. 6B: top sequence (SEQ ID NO:1419) and bottom sequence (SEQ ID NO:1420).

DEFINITIONS

Figure 1A:
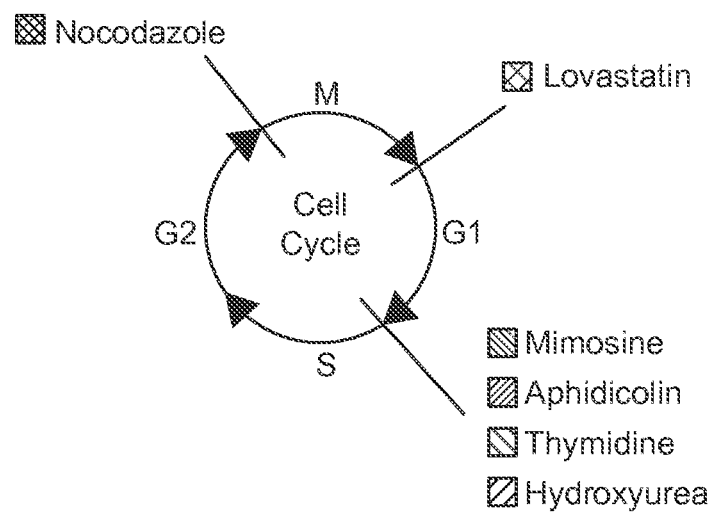
FIG. 1A-1D depict the effect of cell cycle synchronization on NHEJ and HDR frequencies in HEK293T cells.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

A "stem-loop structure" refers to a nucleic acid having a secondary structure that includes a region of nucleotides which are known or predicted to form a double strand (step portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing.

Thus, the stem may include one or more base mismatches. Alternatively, the base-pairing may be exact, i.e. not include any mismatches.

By "hybridizable" or "complementary" or "substantially complementary" it is meant that a nucleic acid (e.g. RNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C) [DNA, RNA]. In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a subject guide RNA molecule is considered complementary to a uracil (U), and vice versa. As such, when a G/U base-pair can be made at a given nucleotide position a protein-binding segment (dsRNA duplex) of a subject guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide) refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a protein-binding protein). In the case of a protein domain-binding protein, it can bind to itself (to form homodimers, homotrimers, etc.) and/or it can bind to one or more molecules of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, or a guide RNA; also called "non-coding" RNA or "ncRNA").

A "protein coding sequence" or a sequence that encodes a particular protein, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

As used herein, a "promoter sequence" is a DNA regulatory region capable of binding RNA polymerase and initiating transcription of a downstream (3' direction) coding or non-coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like. For example, U6 promoters can be used to control the expression of non-coding RNA molecules (e.g., a guide RNA, an activator-RNA, a targeting-RNA, etc.) in eukaryotic cells.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject Cas9 protein in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn, et al. (2010) Nat. Med. 16(10):1161-1166); a serotonin receptor promoter (see, e.g., GenBank S62283); a tyrosine hydroxylase promoter (TH) (see, e.g., Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g., Radovick et al. (1991) Proc. Natl. Acad. Sci. USA 88:3402-3406); an L7 promoter (see, e.g., Oberdick et al. (1990) Science 248:223-226); a DNMT promoter (see, e.g., Bartge et al. (1988) Proc. Natl. Acad. Sci. USA 85:3648-3652); an enkephalin promoter (see, e.g., Comb et al. (1988) EMBO J. 17:3793-3805); a myelin basic protein (MBP) promoter; a $Ca^{2+}$-calmodulin-dependent protein kinase II-alpha (CamKIIα) promoter (see, e.g., Mayford et al. (1996) Proc. Natl. Acad. Sci. USA 93:13250; and Casanova et al. (2001) Genesis 31:37); a CMV enhancer/platelet-derived growth factor-β promoter (see, e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g., Knight et al. (2003) Proc. Natl. Acad. Sci. USA 100:14725); a fatty acid translocase (FAT/CD36) promoter (see, e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g., Mason et al. (1998) Endocrinol. 139:1013; and Chen et al. (1999) Biochem. Biophys. Res. Comm. 262:187); an adiponectin promoter (see, e.g., Kita et al. (2005) Biochem. Biophys. Res. Comm. 331:484; and Chakrabarti (2010) Endocrinol. 151:2408); an adipsin promoter (see, e.g., Platt et al. (1989) Proc. Natl. Acad. Sci. USA 86:7490); a resistin promoter (see, e.g., Seo et al. (2003) Molec. Endocrinol. 17:1522); and the like.

Cardiomyocyte-specific spatially restricted promoters include, but are not limited to control sequences derived from the following genes: myosin light chain-2, α-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22α promoter (see, e.g., Akyürek et al. (2000) Mol. Med. 6:983; and U.S. Pat. No. 7,169,874); a smoothelin promoter (see, e.g., WO 2001/018048); an α-smooth muscle actin promoter; and the like. For example, a 0.4 kb region of the SM22α promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., a Cas9 protein) and/or regulate translation of an encoded polypeptide.

The term "naturally-occurring" or "unmodified" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "chimeric" as used herein as applied to a nucleic acid or polypeptide refers to two components that are defined by structures derived from different sources. For example, where "chimeric" is used in the context of a chimeric polypeptide (e.g., a chimeric Cas9 protein), the chimeric polypeptide includes amino acid sequences that are derived from different polypeptides. A chimeric polypeptide may comprise either modified or naturally-occurring polypeptide sequences (e.g., a first amino acid sequence from a modified or unmodified Cas9 protein; and a second amino acid sequence other than the Cas9 protein). Similarly, "chimeric" in the context of a polynucleotide encoding a chimeric polypeptide includes nucleotide sequences derived from different coding regions (e.g., a first nucleotide sequence encoding a modified or unmodified Cas9 protein; and a second nucleotide sequence encoding a polypeptide other than a Cas9 protein).

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Chimeric polypeptides can be referred to as "fusion variants" or "fusion proteins."

"Heterologous," as used herein, means a nucleotide or polypeptide sequence that is not found in the native nucleic acid or protein, respectively. For example, in a chimeric Cas9 protein, the RNA-binding domain of a naturally-occurring bacterial Cas9 protein (or a variant thereof) may be fused to a heterologous polypeptide sequence (i.e. a polypeptide sequence from a protein other than Cas9 or a polypeptide sequence from another organism). The heterologous polypeptide sequence (also referred to as a "fusion partner") may exhibit an activity (e.g., enzymatic activity) that will also be exhibited by the chimeric Cas9 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 site-directed polypeptide, a variant Cas9 site-directed polypeptide may be fused to a heterologous polypeptide (i.e. a polypeptide other than Cas9), which exhibits an activity that will also be exhibited by the fusion variant Cas9 site-directed polypeptide. A heterologous nucleic acid sequence may be linked to a variant Cas9 site-directed polypeptide (e.g., by genetic engineering) to generate a nucleotide sequence encoding a fusion variant Cas9 site-directed polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target DNA" as used herein is a DNA polynucleotide that comprises a "target site" or "target sequence." The terms "target site" or "target sequence" or "target protospacer DNA" are used interchangeably herein to refer to a nucleic acid sequence present in a target DNA to which a DNA-targeting segment of a subject guide RNA will bind (see FIG. 5A-5B), provided sufficient conditions for binding exist. For example, the target site (or target sequence) 5'-GAGCATATC-3' within a target DNA is targeted by (or is bound by, or hybridizes with, or is complementary to) the RNA sequence 5'-GAUAUGCUC-3'. Suitable DNA/RNA binding conditions include physiological conditions normally present in a cell. Other suitable DNA/RNA binding conditions (e.g., conditions in a cell-free system) are known in the art; see, e.g., Sambrook, supra. The strand of the target DNA that is complementary to and hybridizes with the guide RNA is referred to as the "complementary strand" and the strand of the target DNA that is complementary to the "complementary strand" (and is therefore not complementary to the guide RNA) is referred to as the "noncomplementary strand" or "non-complementary strand."

By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guide RNA and a Cas9 protein is used for targeted double-stranded DNA cleavage. In certain embodiments, a complex comprising a guide RNA and a Cas9 protein is used for targeted cleavage of a single strand of a double-stranded target DNA.

"Nuclease" and "endonuclease" (e.g., DNA nuclease and/or DNA endonuclease) are used interchangeably herein to mean an enzyme which possesses catalytic activity for DNA cleavage.

By "segment" it is meant a segment/section/region of a molecule, e.g., a contiguous stretch of nucleotides of an RNA. A segment can also mean a region/section of a complex such that a segment may comprise regions of more than one molecule. For example, in some cases the protein-binding segment (described below) of a guide RNA is one RNA molecule and the protein-binding segment therefore comprises a region of that RNA molecule. In other cases, the protein-binding segment (described below) of a guide RNA comprises two separate molecules that are hybridized along a region of complementarity. As an illustrative, non-limiting example, a protein-binding segment of a guide RNA that comprises two separate molecules can comprise (i) base pairs 40-75 of a first RNA molecule that is 100 base pairs in length; and (ii) base pairs 10-25 of a second RNA molecule that is 50 base pairs in length. The definition of "segment," unless otherwise specifically defined in a particular context, is not limited to a specific number of total base pairs, is not limited to any particular number of base pairs from a given RNA molecule, is not limited to a particular number of separate molecules within a complex, and may include regions of RNA molecules that are of any total length and may or may not include regions with complementarity to other molecules.

By "cleavage domain" or "active domain" or "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

By "Cas9 polypeptide" or "Cas9 protein" or "site-directed modifying polypeptide" or "RNA-binding site-directed polypeptide" or "RNA-binding site-directed modifying polypeptide" or "site-directed polypeptide" it is meant a polypeptide that binds RNA and is targeted to a specific DNA sequence. A Cas9 protein as described herein is targeted to a specific DNA sequence by the RNA (a guide RNA) to which it is bound. The guide RNA comprises a sequence that is complementary to a target sequence within the target DNA, thus targeting the bound Cas9 protein to a specific location within the target DNA (the target sequence).

Figure 5A:
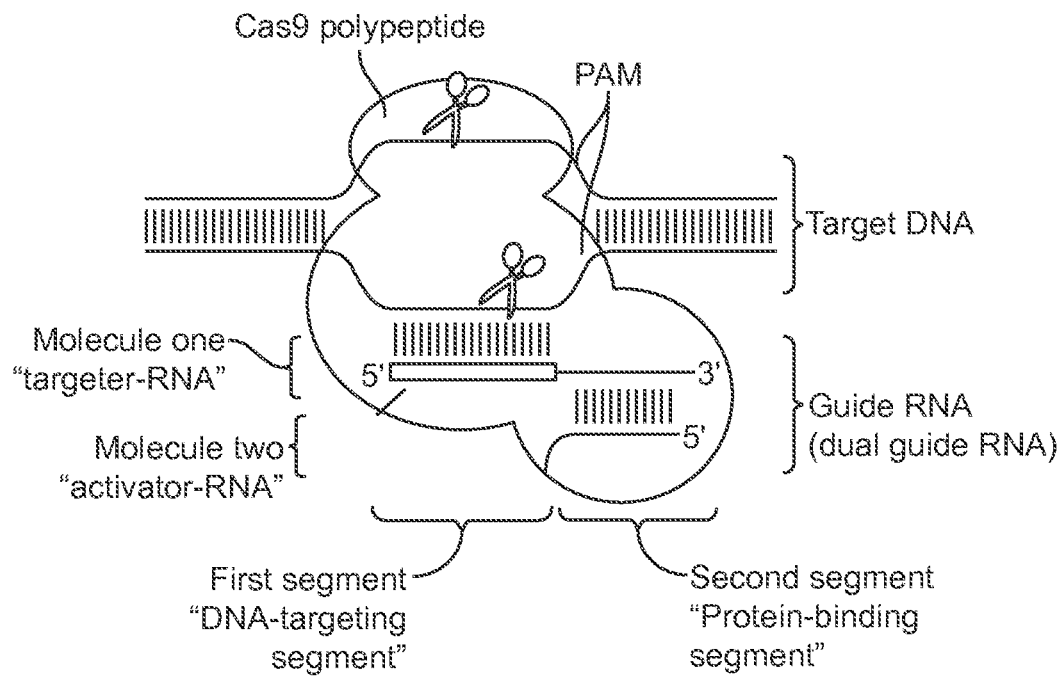
FIG. 5A-5B provide a schematic drawing of a Cas9 targeting complex binding to a target sequence of a target DNA. Panels A and B depict two exemplary guide RNAs (A-dual guide RNA; B-single guide RNA), each associated with a Cas9 protein and with a target DNA.
Figure 5B:
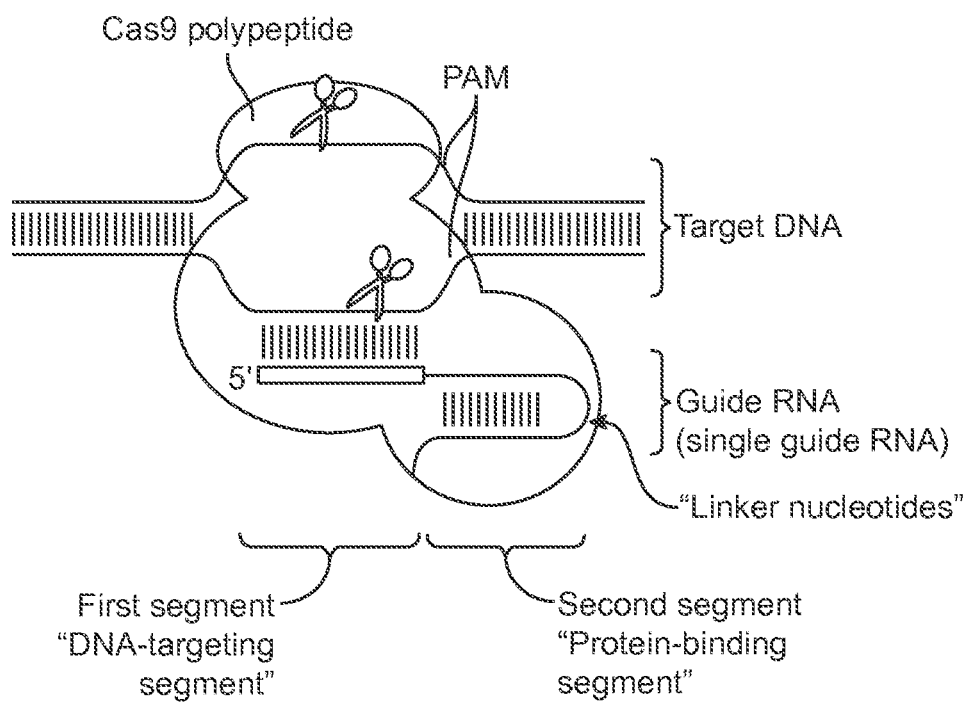

By "guide RNA" it is meant an RNA molecule that binds to a Cas9 protein and targets the Cas9 protein to a specific location within the target DNA (see FIG. 5A-5B). A subject "guide RNA" (also referred to as a "gRNA" or "DNA-targeting RNA" or "DNA-targeting RNA polynucleotide") has two segments: a "DNA-targeting segment" and a "protein-binding segment." The DNA-targeting segment of a guide RNA includes a nucleotide sequence (a "DNA-targeting sequence") that is complementary to a specific sequence within a target DNA (the complementary strand of a target DNA). The protein-binding segment of a guide RNA interacts with a Cas9 protein. The protein-binding segment of a subject guide RNA comprises two complementary stretches of nucleotides that hybridize to one another to form a double stranded RNA duplex (dsRNA duplex).

In some embodiments, a subject guide RNA comprises two separate RNA molecules (RNA polynucleotides: an "activator-RNA" and a "targeter-RNA", see below) and is referred to herein as a "dual guide RNA" or a "double-molecule guide RNA" or a "two-molecule guide RNA." In other embodiments, the subject guide RNA is a single RNA molecule (single RNA polynucleotide) and is referred to herein as a "single guide RNA" or "sgRNA" or "single-molecule guide RNA/" The term}"guide RNA" or "DNA-targeting RNA" or "gRNA" is inclusive, referring both to dual guide RNAs and to single guide RNAs (i.e., sgRNAs).

A subject dual guide RNA comprises a "targeter-RNA" ("crRNA-likeRNA" or "CRISPR RNA" or "crRNA" or "crRNA repeat") molecule and a corresponding "activator-RNA" ("trans-acting CRISPR RNA" or "tracrRNA-like RNA" or "tracrRNA") molecule. A crRNA-like molecule (targeter-RNA) comprises both the DNA-targeting segment (single stranded) of the guide RNA and a stretch ("duplex-forming segment") of nucleotides that contribute to the dsRNA duplex of the protein-binding segment of the guide RNA. A corresponding tracrRNA-like molecule (activator-RNA) also comprises a stretch of nucleotides (duplex-forming segment) that contribute to the dsRNA duplex of the protein-binding segment of the guide RNA. In other words, the duplex-forming segment of a targeter-RNA is complementary to and hybridizes with the duplex-forming segment of an activator-RNA to form the dsRNA duplex of the protein-binding domain of the guide RNA. As such, a targeter-RNA molecule can be said to have a corresponding activator-RNA molecule. The targeter-RNA also provides the targeting segment (the segment that hybridizes with the target DNA) of the guide RNA. Thus, a targeter-RNA and an activator-RNA (as a corresponding pair) hybridize to form a guide RNA. The exact sequence of a given activator-RNA (e.g., a tracrRNA) or targeter-RNA (e.g., a crRNA) molecule can be characteristic of the species in which the RNA molecules are found (or can be derived from such sequences, i.e., truncated, elongated, etc.). Various crRNAs and tracrRNAs are depicted in corresponding complementary pairs e.g., in U.S. patent applications: 20140068797, 20140189896, 20140179006, 20140170753, 20140179770, 20140186958, 20140186919, 20140186843; international applications: WO2013176772, WO2013141680, WO2013142578, WO2014065596, WO2014089290, WO2014099744, WO2014099750, WO2014104878, WO2014093718, WO2014093622, WO2014093655, WO2014093701, WO2014093712, WO2014093635, WO2014093595, WO2014093694, and WO2014093661; and U.S. Pat. Nos. 8,697,359, 8,771,945; all of which are hereby incorporated by reference in their entirety. A subject guide RNA can comprise any corresponding activator-RNA/targeter-RNA pair (e.g., a crRNA/tracrRNA pair).

The term "activator-RNA" is used herein to mean a tracrRNA-like molecule (e.g., of a dual guide RNA). The term "targeter-RNA" is used herein to mean a crRNA-like molecule (e.g., of a dual guide RNA). The term "duplex-forming segment" is used herein to mean the stretch of nucleotides of an activator-RNA or a targeter-RNA that contributes to the formation of the dsRNA duplex by hybridizing to a stretch of nucleotides of a corresponding activator-RNA or targeter-RNA molecule. In other words, an activator-RNA comprises a duplex-forming segment that is complementary to the duplex-forming segment of the corresponding targeter-RNA. As such, an activator-RNA comprises a duplex-forming segment while a targeter-RNA comprises both a duplex-forming segment and the DNA-targeting segment of the guide RNA. Therefore, a subject dual guide RNA can be comprised of any corresponding activator-RNA and targeter-RNA pair.

By "Cas9 targeting complex" it is meant a complex having a Cas9 protein bound to (i.e., interacting with) a guide RNA. A guide RNA and a subject Cas9 protein form a Cas9 targeting complex (i.e., bind via non-covalent interactions). The guide RNA provides target specificity to the complex by comprising a nucleotide sequence that is complementary to a sequence of a target DNA. The Cas9 protein of the complex provides the site-specific activity. In other words, the Cas9 protein is guided to a target DNA sequence (e.g. a target sequence in a chromosomal nucleic acid; a target sequence in an extrachromosomal nucleic acid, e.g. an episomal nucleic acid, a minicircle; a target sequence in a mitochondrial nucleic acid; a target sequence in a chloroplast nucleic acid; a target sequence in a plasmid; etc.) by virtue of its association with the protein-binding segment of the guide RNA. When the Cas9 protein has nuclease activity, site-specific cleavage of the target DNA occurs where the Cas9 targeting complex is localized within the target DNA, i.e., at a specific site (i.e., location) in the target DNA determined by the base-pairing complementarity between the DNA-targeting sequence of the guide RNA and the target In some embodiments, a subject nucleic acid (e.g., a guide RNA, a nucleic acid encoding a guide RNA; a nucleic acid encoding a Cas9 protein; etc.) comprises a modification or sequence that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

In some embodiments, a subject nucleic acid (e.g., a guide RNA, a nucleic acid encoding a guide RNA; a nucleic acid encoding a Cas9 protein; etc.) comprises an additional segment at either the 5' or 3' end that provides for any of the features described above. For example, a suitable third segment can comprise a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and protein complexes); a stability control sequence; a sequence that forms a dsRNA duplex (i.e., a hairpin)); a sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

The terms "host cell" or "target cell" are used herein to denote an in vivo or in vitro eukaryotic cell (a cell from a unicellular or multicellular organism, e.g., a cell line) which can be, or has been, used as a recipient for a subject Cas9 targeting complex. These terms include the progeny of the original cell which has been targeted (e.g., transfected by nucleic acid encoding a guide RNA). It is understood that the progeny of a single cell may not necessarily be completely identical in morphology or in genomic or total DNA complement as the original parent, due to natural, accidental, or deliberate mutation. A target cell can be any eukaryotic cell having DNA that can be targeted by a Cas9 targeting complex (e.g., a eukaryotic single-cell organism, a somatic cell, a germ cell, a stem cell, a plant cell, an algal cell, an animal cell, in invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, a human cell, etc.).

A "genetically modified host cell" (also referred to as a "recombinant host cell") is a host cell into which has been introduced a heterologous nucleic acid, e.g., an expression vector. For example, a subject eukaryotic host cell is a genetically modified eukaryotic host cell (e.g., a mammalian germ cell, a human cell, etc.), by virtue of introduction into the cell of an exogenous nucleic acid (e.g. a guide RNA, nucleic acid encoding a guide RNA, a targeter-RNA, a nucleic acid encoding a targeter-RNA, an activator-RNA, a nucleic acid encoding an activator-RNA, a nucleic acid encoding a Cas9 protein, etc.).

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

By "recombination" it is meant a process of exchange of genetic information between two polynucleotides. As used herein, "homology-directed repair (HDR)" refers to the specialized form DNA repair that takes place, for example, during repair of double-strand breaks in cells. This process requires nucleotide sequence homology, uses a "donor" molecule to template repair of a "target" molecule (i.e., the one that experienced the double-strand break), and leads to the transfer of genetic information from the donor to the target. Homology-directed repair may result in an alteration of the sequence of the target molecule (e.g., insertion, deletion, mutation), if the donor polynucleotide differs from the target molecule and part or all of the sequence of the donor polynucleotide is incorporated into the target DNA. In some embodiments, the donor polynucleotide, a portion of the donor polynucleotide, a copy of the donor polynucleotide, or a portion of a copy of the donor polynucleotide integrates into the target DNA.

By "non-homologous end joining (NHEJ)" it is meant the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods and compositions for site-specific modification of a target DNA, or a protein associated with a target DNA, in a eukaryotic cell. The present disclosure provides methods of binding a target DNA in a eukaryotic cell.

Methods

The present disclosure provides methods of site-specific modification of a target DNA, or a protein associated with a target DNA, in a eukaryotic cell. The present disclosure provides methods of binding a target DNA in a eukaryotic cell. Subject methods of site-specific modification and/or subject methods of binding can include a step of enriching a cell population for cells that are in a desired phase(s) of the cell cycle (e.g., the S-phase, the M-phase, the G0 phase, the G1 phase, the G2 phase, G1/S, G2/M, etc.); and a step of contacting the target DNA with a Cas9 targeting complex (e.g., via introducing into the target eukaryotic cell(s) at least one component of a Cas9 targeting complex). For example, the subject methods include contacting the target DNA in the target cell(s) with: (i) a Cas9 protein; and (ii) a guide RNA comprising: a targeting sequence that hybridizes to a target sequence of the target DNA, and a protein-binding segment that interacts with the Cas9 protein. A step of enriching can include, for example, a cell separation method and/or a cell synchronization method.

In some embodiments, a subject method of site-specific modification and/or a subject method of binding includes a step of blocking a target cell at a desired phase in the cell cycle (e.g., the S-phase, the M-phase, the G0 phase, the G1 phase, the G2 phase, G1/S, G2/M, etc.); and a step of contacting the target DNA with a Cas9 targeting complex (e.g., via introducing into the target eukaryotic cell(s) at least one component of a Cas9 targeting complex). In some cases, blocking a cell at a phase in the cell cycle includes contacting the cell with a cell cycle blocking agent.

In some embodiments, a subject method of site-specific modification and/or a subject method of binding includes a step of blocking a target cell at the S-phase. In some embodiments, a subject method of site-specific modification and/or a subject method of target nucleic acid binding includes a step of blocking a target eukaryotic cell at the M-phase. In some embodiments, a subject method of site-specific modification and/or a subject method of binding includes a step of blocking a target cell at the G0 phase. In some embodiments, a subject method of site-specific modification and/or a subject method of binding includes a step of blocking a target cell at the G1 phase. In some embodiments, a subject method of site-specific modification and/or a subject method of binding includes a step of blocking a target cell at the G2 phase. In some embodiments, a subject method of site-specific modification and/or a subject method of binding includes a step of blocking a target cell at G1/S. In some embodiments, a subject method of site-specific modification and/or a subject method of binding includes a step of blocking a target cell at G2/M.

In some cases, a subject method of site-specific modification and/or a subject method of target nucleic acid binding comprising: a) blocking a target cell at a desired phase in the cell cycle; and b) contacting target DNA in the target cell with (i) a Cas9 protein; and (ii) a guide RNA comprising: a targeting sequence that hybridizes to a target sequence of the target DNA, and a protein-binding segment that interacts with the Cas9 protein increases the efficiency of HDR and/or NHEJ by at least 10%, at least 25%, at least 50%, at least 75%, at least 2-fold, at least 5-fold, at least 10-fold, or more than 10-fold, compared to the efficiency of site-specific modification or target nucleic acid binding carried out in the absence of a cell cycle blocking or enriching step.

The "efficiency" of non-homologous end joining (NHEJ) and/or homology directed repair (HDR) can be calculated by any convenient method. For example, in some cases, efficiency can be expressed in terms of percentage of successful HDR. For example, a restriction digest assay (e.g., using a restriction enzyme such as HindIII) can be used can be used to generate cleavage products and the ratio of products to substrate can be used to calculate the percentage. For example, a restriction enzyme can be used that directly cleaves DNA containing a newly integrated restriction sequence as the result of successful HDR. More cleaved substrate indicates a greater percent HDR (a greater efficiency of HDR). As an illustrative example, a fraction (percentage) of HDR can be calculated using the following equation [(cleavage products)/(substrate plus cleavage products)] (e.g., b+c/a+b+c), where "a" is the band intensity of DNA substrate and "b" and "c" are the cleavage products.

In some cases, efficiency can be expressed in terms of percentage of successful NHEJ. For example, a T7 endonuclease I assay can be used to generate cleavage products and the ratio of products to substrate can be used to calculate the percentage NHEJ. T7 endonuclease I cleaves mismatched heteroduplex DNA which arises from hybridization of wild-type and mutant DNA strands (NHEJ generates small random insertions or deletions (indels) at the site of the original break). More cleavage indicates a greater percent NHEJ (a greater efficiency of NHEJ). As an illustrative example, a fraction (percentage) of NHEJ can be calculated using the following equation: $(1-(1-(b+c/a+b+c))^{1/2}) \times 100$, where "a" is the band intensity of DNA substrate and "b" and "c" are the cleavage products (see Example 1 and see Ran et. al., Cell. 2013 Sep. 12; 154(6):1380-9). This formula is used (instead of the formula used for HDR, see above) because upon re-annealing, one duplex of mutant DNA can produce two duplexes of mutant:wild-type hybrid, doubling the actual NHEJ frequency.

In some cases, a subject method of site-specific modification and/or a subject method of target nucleic acid binding comprising: a) contacting a target cell with a cell cycle blocking agent that blocks the target cell at a desired phase in the cell cycle; and b) contacting target DNA in the target cell with (i) a Cas9 protein; and (ii) a guide RNA comprising: a targeting sequence that hybridizes to a target sequence of the target DNA, and a protein-binding segment that interacts with the Cas9 protein increases the efficiency of HDR and/or NHEJ by at least 10%, at least 25%, at least 50%, at least 75%, at least 2-fold, at least 5-fold, at least 10-fold, or more than 10-fold, compared to the efficiency of site-specific modification or target nucleic acid binding carried out in the absence of the cell cycle blocking agent.

In some cases, a subject method of site-specific modification and/or a subject method of target nucleic acid binding comprises: a) contacting a target cell with a cell cycle blocking agent that blocks the target cell at a desired phase in the cell cycle; and b) contacting target DNA in the target cell with a Cas9 protein/sgRNA complex. In some cases, a subject method of site-specific modification and/or a subject method of target nucleic acid binding comprising: a) contacting a target cell with a cell cycle blocking agent that blocks the target cell at a desired phase in the cell cycle; and b) contacting target DNA in the target cell with a Cas9 protein/sgRNA complex increases the efficiency of HDR and/or NHEJ by at least 10%, at least 25%, at least 50%, at least 75%, at least 2-fold, at least 5-fold, at least 10-fold, or more than 10-fold, compared to the efficiency of site-specific modification or target nucleic acid binding carried out in the absence of the cell cycle blocking agent.

The present disclosure provides a method of site-specific modification of a target DNA, or a protein associated with a target DNA, in a eukaryotic cell, the method comprising: (a) blocking the cell at a desired phase in the cell cycle; and (b) contacting the target DNA in the cell with: (i) a Cas9 protein, and (ii) a guide RNA comprising: a targeting sequence that hybridizes to a target sequence of the target DNA, and a protein-binding domain that interacts with the Cas9 protein. In some cases, a subject method comprises contacting target DNA in the eukaryotic cell with a Cas9 protein/sgRNA complex. In some cases, a subject method of site-specific modification of a target DNA, or a protein associated with a target DNA, in a eukaryotic cell, the method comprises: (a) blocking the cell at S phase; and (b) contacting the target DNA in the cell with: (i) a Cas9 protein, and (ii) a guide RNA comprising: a targeting sequence that hybridizes to a target sequence of the target DNA, and a protein-binding domain that interacts with the Cas9 protein. In some cases, a subject method of site-specific modification of a target DNA, or a protein associated with a target DNA, in a eukaryotic cell, the method comprises: (a) blocking the cell at M phase; and (b) contacting the target DNA in the cell with: (i) a Cas9 protein, and (ii) a guide RNA comprising: a targeting sequence that hybridizes to a target sequence of the target DNA, and a protein-binding domain that interacts with the Cas9 protein.

In some cases, a subject method of site-specific modification and/or a subject method of target nucleic acid binding comprises: a) contacting a target cell with a cell cycle blocking agent that blocks the target cell at a desired phase in the cell cycle; and b) contacting target DNA in the target cell with a Cas9 protein/guide RNA complex (e.g., Cas9 protein/sgRNA; Cas9 protein/dual-guide RNA, etc.). For example, a cell can be contacted with a Cas9 protein/guide RNA complex having a molar ration, of Cas9 protein to guide RNA, in a range of from 5:1 to 1:5 (e.g., from 4:1 to 1:4, from 3:1 to 1:3, from 2:1 to 1:2, from 1.5:1 to 1:1.5, from 1:1 to 1:1.5, or from 1:1.1 to 1:1.3). In some cases, a cell can be contacted with a Cas9 protein/guide RNA complex having a molar ration, of Cas9 protein to guide RNA, of 1:1, 1:1.1, 1:1.2, 1:1.3, or 1:1.4. In some cases, a cell can be contacted with a Cas9 protein/guide RNA complex having a molar ration, of Cas9 protein to guide RNA, of 1:1.2.

In some embodiments, the amount of Cas9 used to generate the targeting complex (Cas9 protein/guide RNA complex) is in a range of from 1 pmol to 500 pmol (e.g., from 10 pmol to 400 pmol, from 10 pmol to 300 pmol, from 10 pmol to 250 pmol, from 10 pmol to 200 pmol, from 20 pmol to 200 pmol, from 20 pmol to 150 pmol, from 30 pmol to 100 pmol, from 50 pmol to 100 pmol, or from 60 pmol to 100 pmol) (e.g., see materials and methods section of Example 1 below).

In some embodiments, a cell can be contacted with an amount of Cas9 protein/guide RNA in a range of from 1 pmol to 500 pmol (e.g., from 10 pmol to 400 pmol, from 10 pmol to 300 pmol, from 10 pmol to 250 pmol, from 10 pmol to 200 pmol, from 20 pmol to 200 pmol, from 20 pmol to 150 pmol, from 30 pmol to 100 pmol, from 50 pmol to 100 pmol, or from 60 pmol to 100 pmol).

Enriching

In some embodiments, subject methods include (i) the step of enriching a cell population for cells that are in a desired phase(s) of the cell cycle, and/or (ii) the step of blocking a cell at a desired phase in the cell cycle. The cell cycle is the series of events that take place in a cell leading to its division and duplication (replication) that produces two daughter cells. Two major phases of the cell cycle are the S phase (DNA synthesis phase), in which DNA duplication occurs, and the M phase (mitosis), in which the chromosomes segregation and cell division occurs. The eukaryotic cell cycle is traditionally divided into four sequential phases: G1, S, G2, and M. G1, S, and G2 together can collectively be referred to as "interphase". Under certain conditions, cells can delay progress through G1 and can enter a specialized resting state known as G0 (G zero), in which they can remain for days, weeks, or even years before resuming proliferation. The period of transition from one state to another can be referred to using a hyphen, for example, G1/S, G2/M, etc. As is known in the art, various checkpoints exist throughout the cell cycle at which a cell can monitor conditions to determine whether cell cycle progression should occur. For example, the G2/M DNA damage checkpoint serves to prevent cells from entering mitosis (M-phase) with genomic DNA damage.

A step of enriching a population of eukaryotic cells for cells in a desired phase of the cell cycle (e.g., G1, S, G2, M, G1/S, G2/M, G0, etc., or any combination thereof), and can be performed using any convenient method (e.g., a cell separation method and/or a cell synchronization method).

In some cases, a subject method includes a step of enriching a population of eukaryotic cells for cells in the G0 phase of the cell cycle. For example, in some cases, a subject method includes: (a) enriching a population of eukaryotic cells for cells in the G0 phase of the cell cycle; and (b) contacting the target DNA with a Cas9 targeting complex (e.g., via introducing into the target eukaryotic cell(s) at least one component of a Cas9 targeting complex)(e.g., contacting the target DNA with (i) a Cas9 protein; and (ii) a guide RNA comprising: a targeting sequence that hybridizes to a target sequence of the target DNA, and a protein-binding segment that interacts with the Cas9 protein).

In some cases, a subject method includes a step of enriching a population of eukaryotic cells for cells in the G1 phase of the cell cycle. For example, in some cases, a subject method includes: (a) enriching a population of eukaryotic cells for cells in the G1 phase of the cell cycle; and (b) contacting the target DNA with a Cas9 targeting complex (e.g., via introducing into the target eukaryotic cell(s) at least one component of a Cas9 targeting complex)(e.g., contacting the target DNA with (i) a Cas9 protein; and (ii) a guide RNA comprising: a targeting sequence that hybridizes to a target sequence of the target DNA, and a protein-binding segment that interacts with the Cas9 protein).

In some cases, a subject method includes a step of enriching a population of eukaryotic cells for cells in the G2 phase of the cell cycle. For example, in some cases, a subject method includes: (a) enriching a population of eukaryotic cells for cells in the G2 phase of the cell cycle; and (b) contacting the target DNA with a Cas9 targeting complex (e.g., via introducing into the target eukaryotic cell(s) at least one component of a Cas9 targeting complex)(e.g., contacting the target DNA with (i) a Cas9 protein; and (ii) a guide RNA comprising: a targeting sequence that hybridizes to a target sequence of the target DNA, and a protein-binding segment that interacts with the Cas9 protein).

In some cases, a subject method includes a step of enriching a population of eukaryotic cells for cells in the S phase of the cell cycle. For example, in some cases, a subject method includes: (a) enriching a population of eukaryotic cells for cells in the S phase of the cell cycle; and (b) contacting the target DNA with a Cas9 targeting complex (e.g., via introducing into the target eukaryotic cell(s) at least one component of a Cas9 targeting complex)(e.g., contacting the target DNA with (i) a Cas9 protein; and (ii) a guide RNA comprising: a targeting sequence that hybridizes to a target sequence of the target DNA, and a protein-binding segment that interacts with the Cas9 protein).

In some cases, a subject method includes a step of enriching a population of eukaryotic cells for cells in the M phase of the cell cycle. For example, in some cases, a subject method includes: (a) enriching a population of eukaryotic cells for cells in the M phase of the cell cycle; and (b) contacting the target DNA with a Cas9 targeting complex (e.g., via introducing into the target eukaryotic cell(s) at least one component of a Cas9 targeting complex)(e.g., contacting the target DNA with (i) a Cas9 protein; and (ii) a guide RNA comprising: a targeting sequence that hybridizes to a target sequence of the target DNA, and a protein-binding segment that interacts with the Cas9 protein).

In some cases, a subject method includes a step of enriching a population of eukaryotic cells for cells in the G1/S transition of the cell cycle. For example, in some cases, a subject method includes: (a) enriching a population of eukaryotic cells for cells in the G1/S transition of the cell cycle; and (b) contacting the target DNA with a Cas9 targeting complex (e.g., via introducing into the target eukaryotic cell(s) at least one component of a Cas9 targeting complex)(e.g., contacting the target DNA with (i) a Cas9 protein; and (ii) a guide RNA comprising: a targeting sequence that hybridizes to a target sequence of the target DNA, and a protein-binding segment that interacts with the Cas9 protein).

In some cases, a subject method includes a step of enriching a population of eukaryotic cells for cells in the G2/M transition of the cell cycle. For example, in some cases, a subject method includes: (a) enriching a population of eukaryotic cells for cells in the G2/M transition of the cell cycle; and (b) contacting the target DNA with a Cas9 targeting complex (e.g., via introducing into the target eukaryotic cell(s) at least one component of a Cas9 targeting complex)(e.g., contacting the target DNA with (i) a Cas9 protein; and (ii) a guide RNA comprising: a targeting sequence that hybridizes to a target sequence of the target DNA, and a protein-binding segment that interacts with the Cas9 protein).

By "enrich" is meant increasing the fraction of desired cells in the resulting cell population. For example, in some cases, enriching includes selecting desirable cells (e.g., cells that are in the desired phase of the cell cycle) away from undesirable cells (e.g., cells that are not in the desired phase of the cell cycle), which can result in a smaller population of cells, but a greater fraction (i.e., higher percentage) of the cells of the resulting cell population will be desirable cells (e.g., cells that are in the desired phase of the cell cycle). Cell separation methods (described below) can be an example of this type of enrichment. In other cases, enriching includes converting undesirable cells (e.g., cells that are not in the desired phase of the cell cycle) into desirable cells (e.g., cells that are in the desired phase of the cell cycle), which can result in a similar size population of cells as the starting population, but a greater fraction of those cells will be desirable cells (e.g., cells that are in the desired phase of the cell cycle). Cell synchronization methods (described below) can be an example of this type of enrichment. In some cases, enrichment can both change the overall size of the resulting cell population (compared to the size of the starting population) and increase the fraction of desirable cells. For example, multiple methods/techniques can be combined (e.g., to improve enrichment, to enrich for cells a more than one desired phase of the cell cycle, etc.).

In some cases, enriching includes a cell separation method. Any convenient cell separation method can be used to enrich for cells that are at various phases of the cell cycle. Suitable cell separation techniques for enrichment of cells at particular phases of the cell cycle include, but are not limited to: (i) mitotic shake-off (M-phase; mechanical separation on the basis of cell adhesion properties, e.g., adherent cells in the mitotic phase detach from the surface upon gentle shaking, tapping, or rinsing); (ii) Countercurrent centrifugal elutriation (CCE) (G1, S, G2/M, and intermediate states; physical separation on the basis of cell size and density); and (iii) flow cytometry and cell sorting (e.g., G0, G1, S, G2/M; physical separation based on specific intracellular, e.g., DNA, content) and cell surface and/or size properties).

Mitotic shake-off generally includes dislodgment of low adhesive, mitotic cells by agitation (see for example, Bey- routhy et. al., PLoS ONE 3, e3943 (2008); Schorl, C. & Sedivy, Methods 41, 143-150 (2007)). CCE generally includes the separation of cells according to their sedimentation velocity in a gravitational field where the liquid containing the cells is made to flow against the centrifugal force with the sedimentation rate of cells being proportional to their size (see for example, Grosse et. al., Prep Biochem Biotechnol. 2012; 42(3):217-33; Banfalvi et. al., Nat. Protoc. 3, 663-673 (2008)). Flow cytometry methods generally include the characterization of cells according to antibody and/or ligand and/or dye-mediated fluorescence and scattered light in a hydrodynamically focused stream of liquid with subsequent electrostatic, mechanical or fluidic switching sorting (see for example, Coquelle et. al., Biochem. Pharmacol. 72, 1396-1404 (2006); Juan et. al., Cytometry 49, 170-175 (2002)). For more information related to cell separation techniques, refer to, for example, Rosner et al., Nat Protoc. 2013 March; 8(3):602-26.

In some cases, enriching includes a cell synchronization method (i.e., synchronizing the cells of a cell population). Cell synchronization is a process by which cells at different stages of the cell cycle within a cell population (i.e., a population of cells in which various individual cells are in different phases of the cycle) are brought into the same phase. Any convenient cell synchronization method can be used in the subject methods to enrich for cells that are at a desired phase(s) of the cell cycle. For example, cell synchronization can be achieved by blocking cells at a desired phase in the cell cycle, which allows the other cells to cycle until they reach the blocked phase. For example, suitable methods of cell synchronization include, but are not limited to: (i) inhibition of DNA replication, DNA synthesis, and/or mitotic spindle formation (e.g., sometimes referred to herein as contacting a cell with a cell cycle blocking composition); (ii) mitogen or growth factor withdrawal (G0, G1, G0/G1; growth restriction-induced quiescence via, e.g., serum starvation and/or amino acid starvation); and (iii) density arrest (G1; cell-cell contact-induced activation of specific transcriptional programs) (see for example, Rosner et al., Nat Protoc. 2013 March; 8(3):602-26 (e.g., see Table 1 of Rosner et al.), which is hereby incorporated by reference in its entirety, and see references cited therein).

Various methods for cell synchronization will be known to one of ordinary skill in the art and any convenient method can be used. For additional methods for cell synchronization (e.g., synchronization of plant cells), see, for example, Sharma, Methods in Cell Science, 1999, Volume 21, Issue 2-3, pp 73-78 ("Synchronization in plant cells—an introduction"); Dolezel et al., Methods in Cell Science, 1999, Volume 21, Issue 2-3, pp 95-107 ("Cell cycle synchronization in plant root meristems"); Kumagai-Sano et al., Nat Protoc. 2006; 1(6):2621-7; and Cools et al., The Plant Journal (2010) 64, 705-714; and Rosner et al., Nat Protoc. 2013 March; 8(3):602-26; all of which are hereby incorporated by reference in their entirety.

Cell Cycle Blocking Compositions

In some embodiments, a cell (or cells of a cell population), is blocked at a desired phase of the cell cycle (e.g., by contacting the cell with a cycle blocking composition). In some embodiments, cells of a cell population are synchronized (e.g., by contacting the cells with a cell cycle blocking composition). A cell cycle blocking composition can include one or more cell cycle blocking agents. The term "cell cycle blocking agent" is used herein to refer to an agent that blocks (e.g., reversibly blocks (pauses), irreversibly blocks) a cell at a particular point in the cell cycle such that the cell cannot proceed further. Suitable cell cycle blocking agents include reversible cell cycle blocking agents. Reversible cell cycle blocking agents do not render the cell permanently blocked. In other words, when reversible cell cycle blocking agent is removed from the cell medium, the cell is free to proceed through the cell cycle. Cell cycle blocking agents are sometimes referred to in the art as cell synchronization agents because when such agents contact a cell population (e.g., a population having cells that are at different stages of the cell cycle), the cells of the population become blocked at the same phase of the cell cycle, thus synchronizing the population of cells relative to that particular phase of the cell cycle. When the cell cycle blocking agent used is reversible, the cells can then be "released" from cell cycle block.

Suitable cell cycle blocking agents include, but are not limited to: nocodazole (G2, M, G2/M; inhibition of microtubule polymerization), colchicine (G2, M, G2/M; inhibition of microtubule polymerization); demecolcine (colcemid) (G2, M, G2/M; inhibition of microtubule polymerization); hydroxyurea (G1, S, G1/S; inhibition of ribonucleotide reductase); aphidicolin (G1, S, G1/S; inhibition of DNA polymerase-α and DNA polymerase-δ); lovastatin (G1; inhibition of HMG-CoA reductase/cholesterol synthesis and the proteasome); mimosine (G1, S, G1/S; inhibition of thymidine, nucleotide biosynthesis, inhibition of Ctf4/chromatin binding); thymidine (G1, S, G1/S; excess thymidine-induced feedback inhibition of DNA replication); latrunculin A (M; delays anaphase onset, actin polymerization inhibitor, disrupts interpolar microtubule stability); and latrunculin B (M; actin polymerization inhibitor).

Suitable cell cycle blocking agents can include any agent that has the same or similar function as the agents above (e.g., an agent that inhibits microtubule polymerization, an agent that inhibits ribonucleotide reductase, an agent that inhibits DNA polymerase-α and/or DNA polymerase-δ, an agent that inhibits HMG-CoA reductase and/or cholesterol synthesis, an agent that inhibits nucleotide biosynthesis, an agent that inhibits DNA replication, i.e., inhibit DNA synthesis, an agent that inhibits initiation of DNA replication, an agent that inhibits deoxycytosine synthesis, an agent that induces excess thymidine-induced feedback inhibition of DNA replication, and agent that disrupts interpolar microtubule stability, an agent that inhibits actin polymerization, and the like). Suitable agents that block G1 can include: staurosporine, dimethyl sulfoxide (DMSO), glycocorticosteroids, and/or mevalonate synthesis inhibitors. Suitable agents that block G2 phase can include CDK1 inhibitors e.g., RO-3306. Suitable agents that block M can include cytochalasin D.

In some cases, suitable cell cycle blocking agents include: cobtorin; dinitroaniline; benefin (benluralin); butralin; dinitramine; ethalfluralin; oryzalin; pendimethalin; trifluralin; amiprophos-methyl; butamiphos dithiopyr; thiazopyr propyzamider-pronamide-tebutam DCPA (chlorthal-dimethyl); anisomycin; alpha amanitin; jasmonic acid; abscisic acid; menadione; cryptogeine; hydrogen peroxide; sodium permanganate; indomethacin; epoxomycin; lactacystein; icrf 193; olomoucine; roscovitine; bohemine; K252a; okadaic acid; endothal; caffeine; MG132; cycline dependent kinase inhibitors; and the like.

For more information regarding cell cycle blocking agents, see Merrill G F, Methods Cell Biol. 1998; 57:229-49, which is hereby incorporated by reference in its entirety.

Cas9 Targeting Complex

The subject methods include a step of contacting the target DNA with a Cas9 targeting complex (e.g., via introducing into the target eukaryotic cell(s) at least one component of a Cas9 targeting complex). For example, the subject methods can include contacting the target DNA in the target cell(s) with: (i) a Cas9 protein; and (ii) a guide RNA comprising: a targeting sequence that hybridizes to a target sequence of the target DNA, and a protein-binding segment that interacts with the Cas9 protein.

Guide RNA

The present disclosure provides a guide RNA that directs the activities of an associated polypeptide (e.g., a Cas9 protein) to a specific target sequence within a target DNA. A subject guide RNA comprises: a first segment (also referred to herein as a "nucleic acid targeting segment", or simply a "targeting segment"); and a second segment (also referred to herein as a "protein-binding segment").

First Segment: Targeting Segment

The first segment of a subject guide RNA comprises a nucleotide sequence that can be complementary to a sequence (a target site) in a target DNA. In other words, the targeting segment of a subject guide RNA can interact with a target DNA in a sequence-specific manner via hybridization (i.e., base pairing). As such, the nucleotide sequence of the targeting segment may vary and can determine the location within the target DNA that the guide RNA and the target DNA will interact. The targeting segment of a subject guide RNA can be modified (e.g., by genetic engineering) to hybridize to any desired sequence (target site) within a target DNA.

The targeting segment can have a length of from about 12 nucleotides to about 100 nucleotides. For example, the targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence (the targeting sequence) of the targeting segment that is complementary to a nucleotide sequence (target site) of the target DNA can have a length of 12 nt or more. For example, the targeting sequence of the targeting segment that is complementary to a target site of the target DNA can have a length of 12 nt or more, 15 nt or more, 18 nt or more, 19 nt or more, 20 nt or more, 25 nt or more, 30 nt or more, 35 nt or more or 40 nt. For example, the targeting sequence of the targeting segment that is complementary to a target sequence of the target DNA can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. The nucleotide sequence (the targeting sequence) of the targeting segment that is complementary to a nucleotide sequence (target site) of the target DNA can have a length of 12 nt or more.

In some cases, the targeting sequence of the targeting segment that is complementary to a target site of the target DNA is 20 nucleotides in length. In some cases, the targeting sequence of the targeting segment that is complementary to a target site of the target DNA is 19 nucleotides in length.

The percent complementarity between the targeting sequence of the targeting segment and the target site of the target DNA can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target DNA is 100% over the seven contiguous 5'-most nucleotides of the target site of the target DNA. In some cases, the percent complementarity between the targeting sequence of the targeting segment and the target site of the target DNA is 60% or more over about 20 contiguous nucleotides. In some cases, the percent complementarity between the targeting sequence of the targeting segment and the target site of the target DNA is 100% over the fourteen contiguous 5'-most nucleotides of the target site of the target DNA and as low as 0% or more over the remainder. In such a case, the targeting sequence can be considered to be 14 nucleotides in length. In some cases, the percent complementarity between the targeting sequence of the targeting segment and the target site of the target DNA is 100% over the seven contiguous 5'-most nucleotides of the target site of the target DNA and as low as 0% or more over the remainder. In such a case, the targeting sequence can be considered to be 20 nucleotides in length.

Second Segment: Protein-Binding Segment

The protein-binding segment of a subject guide RNA interacts with a Cas9 protein. The subject guide RNA guides the bound polypeptide to a specific nucleotide sequence within target DNA via the above mentioned targeting segment. The protein-binding segment of a subject guide RNA comprises two stretches of nucleotides that are complementary to one another. The complementary nucleotides of the protein-binding segment hybridize to form a double stranded RNA duplex (dsRNA) (see FIG. 5A-5B).

A subject dual guide RNA comprises two separate nucleic acid molecules. Each of the two molecules of a subject dual guide RNA comprises a stretch of nucleotides that are complementary to one another such that the complementary nucleotides of the two molecules hybridize to form the double stranded RNA duplex of the protein-binding segment (FIG. 5A).

In some embodiments, the duplex-forming segment of the activator-RNA is 60% or more identical to one of the activator-RNA molecules (e.g., tracrRNA molecules) set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, the duplex-forming segment of the activator-RNA (or the DNA encoding the duplex-forming segment of the activator-RNA) can be 65% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 70% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 75% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 80% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 85% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 90% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 95% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 98% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 99% or more identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator-RNA (or the DNA encoding the duplex-forming segment of the activator-RNA) can be 100% identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, the duplex-forming segment of the targeter-RNA is 60% or more identical to one of the targeter-RNA (e.g., crRNA) sequences set forth in SEQ ID NOs: 563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, the duplex-forming segment of the targeter-RNA (or the DNA encoding the duplex-forming segment of the targeter-RNA) can be 65% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 70% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 75% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 80% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 85% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 90% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 95% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 98% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 99% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter-RNA (or the DNA encoding the duplex-forming segment of the targeter-RNA) can be 100% identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

A dual guide RNA can be designed to allow for controlled (i.e., conditional) binding of a targeter-RNA with an activator-RNA. Because a dual guide RNA is not functional unless both the activator-RNA and the targeter-RNA are bound in a functional complex with Cas9, a dual guide RNA can be inducible (e.g., drug inducible) by rendering the binding between the activator-RNA and the targeter-RNA to be inducible. As one non-limiting example, RNA aptamers can be used to regulate (i.e., control) the binding of the activator-RNA with the targeter-RNA. Accordingly, the activator-RNA and/or the targeter-RNA can include an RNA aptamer sequence.

Aptamers (e.g., RNA aptamers) are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the nucleic acid molecule (e.g., RNA, DNA/RNA hybrid, etc.) of which they are part. RNA aptamers usually comprise a sequence that folds into a particular structure (e.g., a hairpin), which specifically binds a particular drug (e.g., a small molecule). Binding of the drug causes a structural change in the folding of the RNA, which changes a feature of the nucleic acid of which the aptamer is a part. As non-limiting examples: (i) an activator-RNA with an aptamer may not be able to bind to the cognate targeter-RNA unless the aptamer is bound by the appropriate drug; (ii) a targeter-RNA with an aptamer may not be able to bind to the cognate activator-RNA unless the aptamer is bound by the appropriate drug; and (iii) a targeter-RNA and an activator-RNA, each comprising a different aptamer that binds a different drug, may not be able to bind to each other unless both drugs are present. As illustrated by these examples, a dual guide RNA can be designed to be inducible.

Examples of aptamers and riboswitches can be found, for example, in: Nakamura et al., Genes Cells. 2012 May; 17(5):344-64; Vavalle et al., Future Cardiol. 2012 May; 8(3):371-82; Citartan et al., Biosens Bioelectron. 2012 Apr. 15; 34(1):1-11; and Liberman et al., Wiley Interdiscip Rev RNA. 2012 May-June; 3(3):369-84; all of which are herein incorporated by reference in their entirety.

Non-limiting examples of nucleotide sequences that can be included in a dual guide RNA include either of the sequences set forth in SEQ ID NOs:431-562, or complements thereof pairing with any sequences set forth in SEQ ID NOs:563-679, or complements thereof that can hybridize to form a protein binding segment.

A subject single guide RNA comprises two stretches of nucleotides (much like a "targeter-RNA" and an "activator-RNA" of a dual guide RNA) that are complementary to one another, hybridize to form the double stranded RNA duplex (dsRNA duplex) of the protein-binding segment (thus resulting in a stem-loop structure), and are covalently linked by intervening nucleotides ("linkers" or "linker nucleotides"). The targeter-RNA and the activator-RNA can be covalently linked via the 3' end of the targeter-RNA and the 5' end of the activator-RNA. Alternatively, targeter-RNA and the activator-RNA can be covalently linked via the 5' end of the targeter-RNA and the 3' end of the activator-RNA.

The linker of a single guide RNA can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single guide RNA is 4 nt.

An exemplary single guide RNA comprises two complementary stretches of nucleotides that hybridize to form a dsRNA duplex. In some embodiments, one of the two complementary stretches of nucleotides of the single guide RNA (or the DNA encoding the stretch) is 60% or more identical to one of the activator-RNA (e.g., tracrRNA) molecules set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the single guide RNA (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the tracrRNA sequences set forth in SEQ ID NOs:431-562, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide RNA (or the DNA encoding the stretch) is 60% or more identical to one of the targeter-RNA (e.g., crRNA) sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the single guide RNA (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide RNA (or the DNA encoding the stretch) is 60% or more identical to one of the targeter-RNA (e.g., crRNA) sequences or activator-RNA (e.g., tracrRNA) sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the single guide RNA (or the DNA encoding the stretch) can be 65% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide RNA (or the DNA encoding the stretch) can be 70% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide RNA (or the DNA encoding the stretch) can be 75% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides)

One of the two complementary stretches of nucleotides of the single guide RNA (or the DNA encoding the stretch) can be 80% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide RNA (or the DNA encoding the stretch) can be 85% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide RNA (or the DNA encoding the stretch) can be 90% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide RNA (or the DNA encoding the stretch) can be 95% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide RNA (or the DNA encoding the stretch) can be 98% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide RNA (or the DNA encoding the stretch) can be 99% or more identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

One of the two complementary stretches of nucleotides of the single guide RNA (or the DNA encoding the stretch) can be 100% identical to one of the sequences set forth in SEQ ID NOs: 431-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

Appropriate cognate pairs of targeter-RNAs and activator-RNAs can be routinely determined for SEQ ID NOs: 431-679 by taking into account the species name and base-pairing (for the dsRNA duplex of the protein-binding domain). See, for example, U.S. patent applications: 20140068797, 20140189896, 20140179006, 20140170753, 20140179770, 20140186958, 20140186919, 20140186843; international applications: WO2013176772, WO2013141680, WO2013142578, WO2014065596, WO2014089290, WO2014099744, WO2014099750, WO2014104878, WO2014093718, WO2014093622, WO2014093655, WO2014093701, WO2014093712, WO2014093635, WO2014093595, WO2014093694, and WO2014093661; and U.S. Pat. Nos. 8,697,359, 8,771,945 for non-limiting examples of activator-RNA sequences, targeter-RNA sequences, paired activator-RNA/targeter-RNA sequences, and single guide RNA sequences designed from corresponding activator-RNA/targeter-RNA pairs).

The protein-binding segment can have a length of from about 10 nucleotides to about 100 nucleotides. For example, the protein-binding segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

Also with regard to both a subject single guide RNA and to a subject dual guide RNA, the dsRNA duplex of the protein-binding segment can have a length from about 6 base pairs (bp) to about 50 bp. For example, the dsRNA duplex of the protein-binding segment can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the protein-binding segment can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp. In some embodiments, the dsRNA duplex of the protein-binding segment has a length of 36 base pairs. The percent complementarity between the nucleotide sequences that hybridize to form the dsRNA duplex of the protein-binding segment can be 60% or more. For example, the percent complementarity between the nucleotide sequences that hybridize to form the dsRNA duplex of the protein-binding segment can be 65% or more, 70% or more, 75% or more, 80% or more, 85% or more, 90% or more, 95% or more, 98% or more, or 99% or more. In some cases, the percent complementarity between the nucleotide sequences that hybridize to form the dsRNA duplex of the protein-binding segment is 100%.

Stability Control Sequence (e.g., Transcriptional Terminator Segment)

In some embodiments, a guide RNA comprises a stability control sequence. A stability control sequence influences the stability of a nucleic acid (e.g., a guide RNA, a targeter-RNA, an activator-RNA, etc.). One example of a suitable stability control sequence for use with an RNA is a transcriptional terminator segment (i.e., a transcription termination sequence). A transcriptional terminator segment of a subject guide RNA can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

Non-limiting examples of nucleotide sequences that can be included in a stability control sequence (e.g., transcriptional termination segment, or in any segment of the guide RNA to provide for increased stability) include sequences set forth in SEQ ID NO:683-696 and, for example, 5'-UAAUCCCACAGCCGCCAGUUCCGCUGGCG-GCAUUUU-5' (SEQ ID NO:795) (a Rho-independent trp termination site).

Additional Sequences

In some embodiments, a guide RNA comprises an additional segment or segments (in some cases at the 5' end, in some cases the 3' end, in some cases at either the 5' or 3' end, in some cases embedded within the sequence (i.e., not at the 5' and/or 3' end), in some cases at both the 5' end and the 3' end, in some cases embedded and at the 5' end and/or the 3' end, etc). For example, a suitable additional segment can comprise a 5' cap (e.g., a 7-methylguanylate cap ($m^7G$)); a 3' polyadenylated tail (i.e., a 3' poly(A) tail); a ribozyme sequence (e.g. to allow for self-cleavage of a guide RNA (or component of a guide RNA, e.g., a targeter-RNA, an activator-RNA, etc.) and release of a mature PAM-mer in a regulated fashion); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., a direct lable (e.g., direct conjugation to a fluorescent molecule (i.e., fluorescent dye)), conjugation to a moiety that facilitates fluorescent detection, a sequence that allows for fluorescent detection; a modification or sequence that provides a binding site for proteins (e.g., proteins that act on DNA, including transcriptional activator-RNAs, transcriptional repressors, DNA methyltransferases, DNA demethylases, histone acetyltransferases, histone deacetylases, proteins that bind RNA (e.g., RNA aptemers), labeled proteins, fluorescently labeled proteins, and the like); a modification or sequence that provides for increased, decreased, and/or controllable stability; and combinations thereof.

Donor Polynucleotides

In some cases, the subject methods comprise contacting the target DNA with a donor polynucleotide, wherein the donor polynucleotide, a portion of the donor polynucleotide, a copy of the donor polynucleotide, or a portion of a copy of the donor polynucleotide integrates into the target DNA (e.g., via homology-directed repair). In some cases, the method does not comprise contacting the cell with a donor polynucleotide (e.g., resulting in non-homologous end-joining). A donor poly nucleotide can be introduced into a target cell using any convenient technique for introducing nucleic acids into cells.

When it is desirable to insert a polynucleotide sequence into a target DNA sequence, a polynucleotide comprising a donor sequence to be inserted is provided to the cell (e.g., the target DNA is contacted with a donor polynucleotide in addition to a Cas9 targeting complex). By a "donor sequence" or "donor polynucleotide" it is meant a nucleic acid sequence to be inserted at the cleavage site induced by a Cas9 protein. A suitable donor polynucleotide can be single stranded or double stranded. For example, in some cases, a donor polynucleotide is single stranded (e.g., in some cases can be referred to as an oligonucleotide), and in some cases a donor polynucleotide is double stranded (e.g., in some cases can be include two separate oligonucleotides that are hybridized). The donor polynucleotide will contain sufficient homology to a genomic sequence at the cleavage site, e.g. 70%, 80%, 85%, 90%, 95%, or 100% homology with the nucleotide sequences flanking the cleavage site, e.g. within 100 bases or less (e.g., 50 bases or less of the cleavage site, e.g. within 30 bases, within 15 bases, within 10 bases, within 5 bases, or immediately flanking the cleavage site), to support homology-directed repair between it and the genomic sequence to which it bears homology. Approximately 25 nucleotides (nt) or more (e.g., 30 nt or more, 40 nt or more, 50 nt or more, 60 nt or more, 70 nt or more, 80 nt or more, 90 nt or more, 100 nt or more, 150 nt or more, 200 nt or more, etc.) of sequence homology between a donor and a genomic sequence (or any integral value between 10 and 200 nucleotides, or more) can support homology-directed repair. For example, in some cases, the 5' and/or the 3' flanking homology arm (e.g., in some cases both of the flanking homology arms) of a donor polynucleotide can be 30 nucleotides (nt) or more in length (e.g., 40 nt or more, 50 nt or more, 60 nt or more, 70 nt or more, 80 nt or more, 90 nt or more, 100 nt or more, etc.). For example, in some cases, the 5' and/or the 3' flanking homology arm (e.g., in some cases both of the flanking homology arms) of a donor polynucleotide can have a length in a range of from 30 nt to 500 nt (e.g., 30 nt to 400 nt, 30 nt to 350 nt, 30 nt to 300 nt, 30 nt to 250 nt, 30 nt to 200 nt, 30 nt to 150 nt, 30 nt to 100 nt, 30 nt to 90 nt, 30 nt to 80 nt, 50 nt to 400 nt, 50 nt to 350 nt, 50 nt to 300 nt, 50 nt to 250 nt, 50 nt to 200 nt, 50 nt to 150 nt, 50 nt to 100 nt, 50 nt to 90 nt, 50 nt to 80 nt, 60 nt to 400 nt, 60 nt to 350 nt, 60 nt to 300 nt, 60 nt to 250 nt, 60 nt to 200 nt, 60 nt to 150 nt, 60 nt to 100 nt, 60 nt to 90 nt, 60 nt to 80 nt).

Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide."

In some cases, a donor polynucleotide is delivered to the cell (introduced into a cell) as part of viral vector (e.g., an adeno-associated virus (AAV) vector) (e.g., in combination with cell synchronization, in combination with blocking a cell at a desired phase in the cell cycle, etc., as described elsewhere in this disclosure). For example a viral DNA (e.g., AAV DNA) can include a donor polynucleotide sequence (donor sequence) (e.g., a virus, e.g., AAV, can include a DNA molecule that includes a donor polynucleotide sequence). In some cases, a donor polynucleotide is introduced into a cell as a virus (e.g., an AAV, e.g., the donor polynucleotide sequence is present as part of the viral DNA, e.g., AAV DNA) and the Cas9 protein and Cas9 guide RNA are delivered by a different route. For example, in some cases, a donor polynucleotide is introduced into a cell as a virus (e.g., an AAV, e.g., the donor polynucleotide sequence is present as part of the viral DNA, e.g., AAV DNA) and the Cas9 protein and Cas9 guide RNA are delivered as part of a separate expression vector. In some cases, a donor polynucleotide is introduced into a cell as a virus (e.g., an AAV, e.g., the donor polynucleotide sequence is present as part of the viral DNA, e.g., AAV DNA) and the Cas9 protein and Cas9 guide RNA are delivered as part of a ribonucleoprotein complex (RNP) (e.g., described in more detail below). In some cases: (i) a donor polynucleotide is introduced into a cell as a virus (e.g., an AAV, e.g., the donor polynucleotide sequence is present as part of the viral DNA, e.g., AAV DNA), (ii) the Cas9 guide RNA is delivered as either an RNA or DNA encoding the RNA, and (iii) a Cas9 protein is delivered as a protein or as a nucleic acid encoding the protein (e.g., RNA or DNA).

In some cases, a recombinant viral vector (e.g., a recombinant AAV vector) comprising a donor polynucleotide is introduced into a cell before the Cas9-guide RNA RNP is introduced into the cell. For example, in some cases, a recombinant viral vector (e.g., a recombinant AAV vector) comprising a donor polynucleotide is introduced into a cell from 2 hours to 72 hours (e.g., from 2 hours to 4 hours, from 4 hours to 8 hours, from 8 hours to 12 hours, from 12 hours to 24 hours, from 24 hours to 48 hours, or from 48 hours to 72 hours) before the Cas9-guide RNA RNP is introduced into the cell. In some cases, a subject method comprises: a) blocking a cell at a desired phase in the cell cycle; b) contacting the cell with a recombinant viral vector (e.g., a recombinant AAV vector) comprising a donor polynucleotide; and c) contacting the cell with a Cas9-guide RNA RNP.

The present disclosure provides kits and compositions that include (i) a viral vector (e.g., a viral DNA, a virion, etc.)(e.g., an AAV vector) that includes the donor polynucleotide (i.e., the viral DNA includes the donor sequence); (ii) a Cas9 protein or nucleic acid encoding the protein; (iii) a Cas9 guide RNA or a DNA encoding the Cas9 guide RNA; and/or (iv) a cell cycle blocking composition (e.g., a composition that includes at least one of nocodazole, hydroxyurea; colchicine; demecolcine (colcemid); lovastatin; mimosine; thymidine; aphidicolin; latrunculin A; and latrunculin B). The present disclosure provides kits and compositions that include (i) a viral vector (e.g., a viral DNA, a virion, etc.)(e.g., an AAV vector) that includes the donor polynucleotide (i.e., the viral DNA includes the donor sequence); (ii) an RNP that includes a Cas9 protein and a Cas9 guide RNA; and/or (iii) a cell cycle blocking composition (e.g., a composition that includes at least one of nocodazole, hydroxyurea; colchicine; demecolcine (colcemid); lovastatin; mimosine; thymidine; aphidicolin; latrunculin A; and latrunculin B).

Cas9 Proteins

A suitable guide RNA and a suitable Cas9 protein form a Cas9 targeting complex. The guide RNA provides target specificity to the complex by comprising a nucleotide sequence that is complementary to a sequence (the target site) of a target nucleic acid (as noted above). The Cas9 protein of the complex provides the site-specific activity. In other words, the Cas9 protein is guided to a target site within a target nucleic acid sequence (e.g. a chromosomal sequence or an extrachromosomal sequence, e.g. an episomal sequence, a minicircle sequence, a mitochondrial sequence, a chloroplast sequence, etc.) by virtue of its association with the protein-binding segment of the guide RNA (described above).

A suitable Cas9 protein can bind and/or modify (e.g., cleave, methylate, demethylate, etc.) a target nucleic acid and/or a polypeptide associated with target nucleic acid (e.g., methylation or acetylation of a histone tail). A Cas9 protein is also referred to herein as a "site-directed polypeptide."

In some cases, the Cas9 protein is a naturally-occurring polypeptide (e.g., naturally occurs in bacterial and/or archaeal cells). In other cases, the Cas9 protein is not a naturally-occurring polypeptide (e.g., the Cas9 protein is a variant Cas9 protein, a chimeric polypeptide as discussed below, and the like).

Exemplary Cas9 proteins are set forth in SEQ ID NOs: 1-259, and 795-1346 as a non-limiting and non-exhaustive list of Cas9 endonucleases. Naturally occurring Cas9 proteins bind a guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A suitable Cas9 protein comprises two portions, an RNA-binding portion and an activity portion. An RNA-binding portion interacts with a guide RNA. An activity portion exhibits site-directed enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases the activity portion exhibits reduced nuclease activity relative to the corresponding portion of a wild type Cas9 protein. In some cases, the activity portion is enzymatically inactive. The activity portion is a general term meant to encompass all parts of the Cas9 protein that exhibits an activity (e.g., nuclease activity). Thus, while Cas9 is known to have two domains that function as nuclease domains, and the domains are separated from each other in the primary amino acid sequence, the domains can be collectively referred to as an activity domain (activity portion). In some cases, the Cas9 polypeptide has an activity portion that is provided by a heterologous sequence (e.g., a methylation activity).

Assays to determine whether a protein has an RNA-binding portion interacts with a subject guide RNA can be any convenient binding assay that tests for binding between a protein and a nucleic acid. Exemplary binding assays will be known to one of ordinary skill in the art and can be found for example in U.S. patent applications: 20140068797, 20140189896, 20140179006, 20140170753, 20140179770, 20140186958, 20140186919, 20140186843; international applications: WO2013176772, WO2013141680, WO2013142578, WO2014065596, WO2014089290, WO2014099744, WO2014099750, WO2014104878, WO2014093718, WO2014093622, WO2014093655, WO2014093701, WO2014093712, WO2014093635, WO2014093595, WO2014093694, and WO2014093661; and U.S. Pat. Nos. 8,697,359, 8,771,945; all of which are hereby incorporated by reference in their entirety. Suitable assays include, without limitation, binding assays (e.g., gel shift assays) that include adding a guide RNA and a Cas9 protein to a target nucleic acid.

Assays to determine whether a protein has an activity portion (e.g., to determine if the polypeptide has nuclease activity that cleave a target nucleic acid) can be any convenient nucleic acid cleavage assay that tests for nucleic acid cleavage. Exemplary cleavage assays can be found in U.S. patent applications: 20140068797, 20140189896, 20140179006, 20140170753, 20140179770, 20140186958, 20140186919, 20140186843; international applications: WO2013176772, WO2013141680, WO2013142578, WO2014065596, WO2014089290, WO2014099744, WO2014099750, WO2014104878, WO2014093718, WO2014093622, WO2014093655, WO2014093701, WO2014093712, WO2014093635, WO2014093595, WO2014093694, and WO2014093661; and U.S. Pat. Nos. 8,697,359, 8,771,945. Suitable assays can include cleavage assays that include adding a guide RNA and a Cas9 protein to a target nucleic acid. In some cases, a PAM-mer is also added (e.g., in some cases when the target nucleic acid is a single stranded nucleic acid).

In some cases, a subject Cas9 protein (e.g., a chimeric Cas9 protein) has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other cases, a suitable Cas9 protein (a chimeric Cas9 protein) has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologs from a wide variety of species have been identified and the proteins share only a few identical amino acids. The identified Cas9 orthologs have the same domain architecture with a central HNH endonuclease domain and a split RuvC/RNaseH domain. Cas9 proteins share 4 key motifs with a conserved architecture. Motifs 1, 2, and 4 are RuvC like motifs while motif 3 is an HNH-motif. In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence (e.g., SEQ ID NOs:260-263, respectively, as depicted in Table 1), or to the corresponding portions in any of the amino acid sequences set forth in SEQ ID NOs:1-256 and 795-1346. Additional Cas9 protein sequences can be found in U.S. patent applications: 20140068797, 20140189896, 20140179006, 20140170753, 20140179770, 20140186958, 20140186919, 20140186843; international applications: WO2013176772, WO2013141680, WO2013142578, WO2014065596, WO2014089290, WO2014099744, WO2014099750, WO2014104878, WO2014093718, WO2014093622, WO2014093655, WO2014093701, WO2014093712, WO2014093635, WO2014093595, WO2014093694, and WO2014093661; and U.S. Pat. Nos. 8,697,359, 8,771,945.

In some cases, a suitable Cas9 protein comprises an amino acid sequence having 4 motifs, each of motifs 1-4 having 60% or more amino acid sequence identity to motifs 1-4 of the SEQ ID NOs:260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 70% or more amino acid sequence identity to motifs 1-4 of the Cas9 amino acid sequences set forth in SEQ ID NOs: 260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 75% or more amino acid sequence identity to motifs 1-4 of the Cas9 amino acid sequences set forth in SEQ ID NOs: 260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 80% or more amino acid sequence identity to motifs 1-4 of the Cas9 amino acid sequences set forth in SEQ ID NOs: 260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 85% or more amino acid sequence identity to motifs 1-4 of the Cas9 amino acid sequences set forth in SEQ ID NOs: 260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 90% or more amino acid sequence identity to motifs 1-4 of the Cas9 amino acid sequences set forth in SEQ ID NOs: 260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 95% or more amino acid sequence identity to motifs 1-4 of the Cas9 amino acid sequences set forth in SEQ ID NOs: 260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 99% or more amino acid sequence identity to motifs 1-4 of the Cas9 amino acid sequences set forth in SEQ ID NOs: 260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 100% amino acid sequence identity to motifs 1-4 of the Cas9 amino acid sequences set forth in SEQ ID NOs:260-263, respectively, as depicted in Table 1, or to the corresponding portions in any of the amino acid sequences set forth in SEQ ID NOs:1-256 and 795-1346.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 60% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 70% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 75% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 80% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 85% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 90% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 95% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 99% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a suitable Cas9 protein comprises an amino acid sequence having 100% amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a Cas9 protein or as part of a chimeric Cas9 protein of the subject methods.

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1(SEQ ID NOs:260-263), or to the corresponding portions in any of the amino acid sequences set forth as SEQ ID NOs:1-256 and 795-1346.

As used herein, the term "Cas9 protein" encompasses the term "variant Cas9 protein"; and the term "variant Cas9 protein" encompasses the term "chimeric Cas9 protein."

Variant Cas9 Proteins

In some cases, a method of the present disclosure involves use of a variant Cas9 protein. A variant Cas9 polypeptide has an amino acid sequence that is different by one amino acid (e.g., has a deletion, insertion, substitution, fusion) when compared to the amino acid sequence of a wild type Cas9 protein. In some instances, the variant Cas9 polypeptide has an amino acid change (e.g., deletion, insertion, or substitution) that reduces the nuclease activity of the Cas9 polypeptide. For example, in some instances, the variant Cas9 polypeptide has less than 50%, less than 40%, less than 30%, less than 20%, less than 10%, less than 5%, or less than 1% of the nuclease activity of the corresponding wild-type Cas9 protein. In some cases, the variant Cas9 protein has no substantial nuclease activity. When a subject Cas9 protein is a variant Cas9 protein that has no substantial nuclease activity, it can be referred to as "dCas9."

In some cases (e.g., for use in methods of modifying a target DNA, in methods of binding to a target DNA, etc.), a variant Cas9 protein has reduced nuclease activity. For example, a variant Cas9 protein suitable for use in a binding method of the present disclosure exhibits less than about 20%, less than about 15%, less than about 10%, less than about 5%, less than about 1%, or less than about 0.1%, of the endonuclease activity of a wild-type Cas9 protein, e.g., a wild-type Cas9 protein comprising an amino acid sequence as set forth in SEQ ID NO:8.

In some cases (e.g., for use in methods of modifying a target DNA, in methods of binding to a target DNA, etc.), a variant Cas9 protein can cleave the complementary strand of a target DNA but has reduced ability to cleave the non-complementary strand of a double stranded target DNA. For example, the variant Cas9 protein can have a mutation (amino acid substitution) that reduces the function of the RuvC domain. As a non-limiting example, in some embodiments, a variant Cas9 protein has a D10A (aspartate to alanine at amino acid position 10 of SEQ ID NO:8 mutation (or the corresponding mutation of any of the proteins presented in SEQ ID NOs:1-256 and 795-1346) and can therefore cleave the complementary strand of a double stranded target DNA but has reduced ability to cleave the non-complementary strand of a double stranded target DNA (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096): 816-21).

In some cases (e.g., for use in methods of modifying a target DNA, in methods of binding to a target DNA, etc.), a variant Cas9 protein can cleave the non-complementary strand of a double stranded target DNA but has reduced ability to cleave the complementary strand of the target DNA. For example, the variant Cas9 protein can have a mutation (amino acid substitution) that reduces the function of the HNH domain (RuvC/HNH/RuvC domain motifs). As a non-limiting example, in some embodiments, the variant Cas9 protein has an H840A (histidine to alanine at amino acid position 840) mutation (or the corresponding mutation of any of the proteins set forth as SEQ ID NOs:1-256 and 795-1346) and can therefore cleave the non-complementary strand of the target DNA but has reduced ability to cleave the complementary strand of the target DNA (thus resulting in a SSB instead of a DSB when the variant Cas9 protein cleaves a double stranded target DNA). Such a Cas9 protein has a reduced ability to cleave a target DNA (e.g., a single stranded target DNA) but retains the ability to bind a target DNA (e.g., a single stranded target DNA).

In some cases (e.g., for use in methods of binding to a target DNA), a variant Cas9 protein has a reduced ability to cleave both the complementary and the non-complementary strands of a double stranded target DNA. As a non-limiting example, in some cases, the variant Cas9 protein harbors both the D10A and the H840A mutations (or the corresponding mutations of any of the proteins set forth as SEQ ID NOs:1-256 and 795-1346) such that the polypeptide has a reduced ability to cleave both the complementary and the non-complementary strands of a double stranded target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors W476A and W1126A mutations (or the corresponding mutations of any of the proteins set forth as SEQ ID NOs:1-256 and 795-1346) such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors P475A, W476A, N477A, D1125A, W1126A, and D1127A mutations (or the corresponding mutations of any of the proteins set forth as SEQ ID NOs:1-256 and 795-1346) such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors H840A, W476A, and W1126A, mutations (or the corresponding mutations of any of the proteins set forth as SEQ ID NOs:1-256 and 795-1346) such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors H840A, D10A, W476A, and W1126A, mutations (or the corresponding mutations of any of the proteins set forth as SEQ ID NOs:1-256 and 795-1346) such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors, H840A, P475A, W476A, N477A, D1125A, W1126A, and D1127A mutations (or the corresponding mutations of any of the proteins set forth as SEQ ID NOs:1-256 and 795-1346) such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors D10A, H840A, P475A, W476A, N477A, D1125A, W1126A, and D1127A mutations (or the corresponding mutations of any of the proteins set forth as SEQ ID NOs:1-256 and 795-1346) such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

In some cases, when a variant Cas9 protein harbors W476A and W1126A mutations (or the corresponding mutations of any of the proteins set forth as SEQ ID NOs:1-256 and 795-1346); or when the variant Cas9 protein harbors P475A, W476A, N477A, D1125A, W1126A, and D1127A mutations (or the corresponding mutations of any of the proteins set forth as SEQ ID NOs:1-256 and 795-1346), the variant Cas9 protein does not bind efficiently to a PAM sequence. Thus, in some such cases, when such a variant Cas9 protein is used in a method of binding, the method need not include a PAM-mer. In other words, in some cases, when such a variant Cas9 protein is used in a method of binding, the method can include a guide RNA, but the method can be performed in the absence of a PAM-mer (and the specificity of binding is therefore provided by the targeting segment of the guide RNA).

Other residues can be mutated to achieve the above effects (i.e. inactivate one or the other nuclease portions). As non-limiting examples, residues D10, G12, G17, E762, H840, N854, N863, H982, H983, A984, D986, and/or A987 (or the corresponding mutations of any of the proteins set forth as SEQ ID NOs:1-256 and 795-1346) can be altered (i.e., substituted). Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or A987 mutation, e.g., D10A, G12A, G17A, E762A, H840A, N854A, N863A, H982A, H983A, A984A, and/or D986A), the variant Cas9 protein can still bind to target DNA in a site-specific manner (because it is still guided to a target DNA sequence by a guide RNA) as long as it retains the ability to interact with the guide RNA.

TABLE 1

Table 1 lists 4 motifs that are present in Cas9 sequences from various species. The amino acids listed here are from the Cas9 from *S. pyogenes* (SEQ ID NO: 8.

| Motif # | Motif | Amino acids (residue #s) | Highly conserved |
|---|---|---|---|
| 1 | RuvC-like I | IGLDIGTNSVGWAVI (7-21) (SEQ ID NO: 260) | D10, G12, G17 |
| 2 | RuvC-like II | IVIEMARE (759-766) (SEQ ID NO: 261) | E762 |
| 3 | HNH-motif | DVDHIVPQSFLKDDSIDNKVLTRSDKN (837-863) (SEQ ID NO: 262) | H840, N854, N863 |
| 4 | RuvC-like II | HHAHDAYL (982-989) (SEQ ID NO: 263) | H982, H983, A984, D986, A987 |

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 70% or more amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 75% or more amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 80% or more amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 85% or more amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 90% or more amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 95% or more amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 99% or more amino acid sequence identity to motifs 1-4 of the Cas9 amino acid sequence set forth in SEQ ID NOs:260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 4 motifs, each of motifs 1-4 having 100% amino acid sequence identity to motifs 1-4 of the Cas9 amino acid sequence set forth in SEQ ID NOs: 260-263, respectively, as depicted in Table 1, or to the corresponding portions in any of the amino acid sequences set forth in SEQ ID NOs:1-256 and 795-1346.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 60% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 70% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 75% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 80% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 85% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 90% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 95% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 99% or more amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

In some cases, a suitable variant Cas9 protein comprises an amino acid sequence having 100% amino acid sequence identity to amino acids 7-166 or 731-1003 of the Cas9 amino acid sequence set forth in SEQ ID NO:8, or to the corresponding portions in any of the amino acid sequences set forth as SEQ ID NOs:1-256 and 795-1346. Any Cas9 protein as defined above can be used as a variant Cas9 protein or as part of a chimeric variant Cas9 protein of the subject methods.

Chimeric Polypeptides (Fusion Polypeptides)

In some embodiments, a variant Cas9 protein is a chimeric Cas9 protein (also referred to herein as a fusion polypeptide, e.g., a "Cas9 fusion polypeptide"). A Cas9 fusion polypeptide can bind and/or modify a target DNA (e.g., cleave, methylate, demethylate, etc.) and/or a polypeptide associated with target DNA (e.g., methylation, acetylation, etc., of, for example, a histone tail).

A Cas9 fusion polypeptide is a variant Cas9 protein by virtue of differing in sequence from a wild type Cas9 protein. A Cas9 fusion polypeptide is a Cas9 protein (e.g., a wild type Cas9 protein, a variant Cas9 protein, a variant Cas9 protein with reduced nuclease activity (as described above), and the like) fused to a covalently linked heterologous polypeptide (also referred to as a "fusion partner"). In some cases, a Cas9 fusion polypeptide is a variant Cas9 protein with reduced nuclease activity (e.g., cleaves the complementary strand of the target DNA but does not cleave the non-complementary strand; cleaves the non-complementary strand of the target DNA but does not cleave the complementary strand; does not cleave either the complementary strand for the non-complementary strand if target DNA (dCas9); as described in more detail in the section related to variant Cas9 polypeptides) fused to a covalently linked heterologous polypeptide.

In some cases, the heterologous polypeptide exhibits (and therefore provides for) an activity (e.g., an enzymatic activity) that will also be exhibited by the Cas9 fusion polypeptide (e.g., methyltransferase activity, acetyltransferase activity, kinase activity, ubiquitinating activity, etc.). In some such cases, a method of binding, e.g., where the Cas9 protein is a variant Cas9 protein having a fusion partner (i.e., having a heterologous polypeptide) with an activity (e.g., an enzymatic activity) that modifies the target DNA, the method can also be considered to be a method of modifying the target DNA. In some cases, a method of binding a target DNA can result in modification of the target DNA. Thus, in some cases, a method of binding a target DNA can be a method of modifying the target DNA.

In some cases, a Cas9 protein has a heterologous sequence that provides for subcellular localization (i.e., the heterologous sequence is a subcellular localization sequence (e.g., a nuclear localization signal (NLS) for targeting to the nucleus, a sequence to keep the fusion protein out of the nucleus (e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a variant Cas9 does not include a NLS so that the protein is not targeted to the nucleus (which can be advantageous, e.g., when the target DNA is an RNA that is present in the cyosol). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target DNA (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a Cas9 fusion polypeptide to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some cases, a suitable degron is constitutive such that the degron exerts its influence on protein stability independent of experimental control (i.e., the degron is not drug inducible, temperature inducible, etc.) In some cases, the degron provides the variant Cas9 protein with controllable stability such that the variant Cas9 protein can be turned "on" (i.e., stable) or "off" (i.e., unstable, degraded) depending on the desired conditions. For example, if the degron is a temperature sensitive degron, the variant Cas9 protein may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1).: Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well-characterized and tested in both cells and animals. Thus, fusing Cas9 (e.g., wild type Cas9; variant Cas9; variant Cas9 with reduced nuclease activity, e.g., dCas9; and the like) to a degron sequence produces a "tunable" and "inducible" Cas9 protein. Any of the fusion partners described herein can be used in any desirable combination. As one non-limiting example to illustrate this point, a Cas9 fusion protein (i.e., a chimeric Cas9 protein) can comprise a YFP sequence for detection, a degron sequence for stability, and transcription activator sequence to increase transcription of the target DNA. A suitable reporter protein for use as a fusion partner for a Cas9 protein (e.g., wild type Cas9, variant Cas9, variant Cas9 with reduced nuclease function, etc.), includes, but is not limited to, the following exemplary proteins (or functional fragment thereof): his3, β-galactosidase, a fluorescent protein (e.g., GFP, RFP, YFP, cherry, tomato, etc., and various derivatives thereof), luciferase, β-glucuronidase, and alkaline phosphatase. Furthermore, the number of fusion partners that can be used in a Cas9 fusion protein is unlimited. In some cases, a Cas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Examples of various additional suitable fusion partners (or fragments thereof) for a subject variant Cas9 protein include, but are not limited to those described in the PCT patent applications: WO2010075303, WO2012068627, and WO2013155555 which are hereby incorporated by reference in their entirety.

Suitable fusion partners include, but are not limited to, a polypeptide that provides an activity that indirectly increases transcription by acting directly on the target DNA or on a polypeptide (e.g., a histone, a DNA-binding protein, an RNA-binding protein, an RNA editing protein, etc.) associated with the target DNA. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target DNA (e.g., a transcription activator or a fragment thereof, a protein or fragment thereof that recruits a transcription activator, a small molecule/drug-responsive transcription and/or translation regulator, a translation-regulating protein, etc.).

Non-limiting examples of fusion partners to accomplish increased or decreased transcription include, e.g., transcription activator and transcription repressor domains (e.g., the Krüppel associated box (KRAB or SKD); the Mad mSIN3 interaction domain (SID); the ERF repressor domain (ERD), etc). In some such cases, a Cas9 fusion protein is targeted by the guide RNA to a specific location (i.e., sequence) in the target DNA and exerts locus-specific regulation such as blocking RNA polymerase binding to a promoter (which selectively inhibits transcription activator function), and/or modifying the local chromatin status (e.g., when a fusion sequence is used that modifies the target DNA or modifies a polypeptide associated with the target DNA). In some cases, the changes are transient (e.g., transcription repression or activation). In some cases, the changes are inheritable (e.g., when epigenetic modifications are made to the target DNA or to proteins associated with the target DNA, e.g., nucleosomal histones).

In some embodiments, the heterologous sequence can be fused to the C-terminus of the Cas9 protein. In some embodiments, the heterologous sequence can be fused to the N-terminus of the Cas9 protein. In some embodiments, the heterologous sequence can be fused to an internal portion (i.e., a portion other than the N- or C-terminus) of the Cas9 protein.

In some embodiments, a Cas9 protein (e.g., a wild type Cas9, a variant Cas9, a variant Cas9 with reduced nuclease activity, etc.) can be linked to a fusion partner via a peptide spacer.

Nucleic Acids Encoding a Targeter-RNA, an Activator-RNA, a Single Guide RNA, and/or a Cas9 Protein Methods of the present disclosure include contacting a target cell (or contacting enriched cells of a cell population) with a Cas9 targeting complex. Contacting can include introducing into a cell at least one of: (a) a single guide RNA, (b) a DNA polynucleotide encoding a single guide RNA, (c) a targeter-RNA, (d) a DNA polynucleotide encoding a targeter-RNA, (e) an activator-RNA, (f) a DNA polynucleotide encoding an activator-RNA, (g) a Cas9 protein, and (h) a nucleic acid encoding a Cas9 protein.

In some cases, the cell already contains a component of the Cas9 targeting complex (or a nucleic acid encoding a component), and one performing the method therefore needs only to introduce into the cell the component(s) that are missing. For example, if the target cell already has a nucleic acid encoding a Cas9 protein, the one performing the method may only need to introduce the guide RNA component(s) of the Cas9 targeting complex.

In some cases, a component of a Cas9 targeting complex (a targeter-RNA, an activator-RNA, a guide RNA (e.g., a single guide RNA), and/or a Cas9 protein) is provided as a nucleic acid encoding the component. In some embodiments, a subject nucleic acid is an expression vector, e.g., a recombinant expression vector. As such, in some embodiments, a subject method involves contacting a target DNA (e.g., via introducing into a target cell or a population of cells) with a nucleic acid encoding a targeter-RNA, an activator-RNA, a guide RNA (e.g., a single guide RNA), and/or a Cas9 protein.

In some embodiments a cell comprising a target DNA is in vitro and/or ex vivo. In some embodiments a cell comprising a target DNA is in vivo. Suitable nucleic acids comprising nucleotide sequences encoding a targeter-RNA, an activator-RNA, a guide RNA (e.g., a single guide RNA), and/or a Cas9 protein include expression vectors (e.g., recombinant expression vectors).

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, a nucleotide sequence encoding a targeter-RNA, an activator-RNA, a guide RNA (e.g., a single guide RNA), and/or a Cas9 protein is operably linked to a control element, e.g., a transcriptional control element, such as a promoter (e.g. a promoter functional in a eukaryotic cell). In some embodiments, a nucleotide sequence encoding a component of a Cas9 targeting complex is operably linked to multiple control elements that allow expression of the nucleotide sequence encoding a PAM-mer, and/or a guide RNA and/or a Cas9 protein in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that are fused to the Cas9 protein, thus resulting in a chimeric polypeptide.

In some embodiments, a nucleotide sequence encoding a component of a Cas9 targeting complex is operably linked to an inducible promoter In some embodiments, a nucleotide sequence encoding a component of a Cas9 targeting complex is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like. U6 promoters are useful for expression non-coding RNAs (e.g., targeter-RNAs, activator-RNAs, single guide RNAs) in eukaryotic cells.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject Cas9 protein in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn, et al. (2010) Nat. Med. 16(10):1161-1166); a serotonin receptor promoter (see, e.g., GenBank S62283); a tyrosine hydroxylase promoter (TH) (see, e.g., Oh et al. (2009) Gene Ther 16:437; Sasaoka et al. (1992) Mol. Brain Res. 16:274; Boundy et al. (1998 J. Neurosci. 18:9989; and Kaneda et al. (1991) Neuron 6:583-594); a GnRH promoter (see, e.g., Radovick et al. (1991) Proc. Natl. Acad. Sci. USA 88:3402-3406); an L7 promoter (see, e.g., Oberdick et al. (1990) Science 248:223-226); a DNMT promoter (see, e.g., Bartge et al. (1988 Proc. Natl. Acad. Sci. USA 85:3648-3652); an enkephalin promoter (see, e.g., Comb et al. (1988 EMBO J. 17:3793-3805); a myelin basic protein (MBP) promoter; a Ca2+-calmodulin-dependent protein kinase II-alpha (CamKIIα) promoter (see, e.g., Mayford et al. (1996) Proc. Natl. Acad. Sci. USA 93:13250; and Casanova et al. (2001) Genesis 31:37); a CMV enhancer/platelet-derived growth factor-β promoter (see, e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g., Knight et al. (2003) Proc. Natl. Acad. Sci. USA 100:14725); a fatty acid translocase (FAT/CD36) promoter (see, e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g., Mason et al. (1998 Endocrinol. 139:1013; and Chen et al. (1999) Biochem. Biophys. Res. Comm. 262:187); an adiponectin promoter (see, e.g., Kita et al. (2005) Biochem. Biophys. Res. Comm. 331:484; and Chakrabarti (2010) Endocrinol. 151:2408; an adipsin promoter (see, e.g., Platt et al. (1989) Proc. Natl. Acad. Sci. USA 86:7490); a resistin promoter (see, e.g., Seo et al. (2003) Molec. Endocrinol. 17:1522); and the like.

Cardiomyocyte-specific spatially restricted promoters include, but are not limited to control sequences derived from the following genes: myosin light chain-2, α-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22α promoter (see, e.g., Akyürek et al. (2000) Mol. Med. 6:983; and U.S. Pat. No. 7,169,874); a smoothelin promoter (see, e.g., WO 2001/018048; an α-smooth muscle actin promoter; and the like. For example, a 0.4 kb region of the SM22α promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

Methods of introducing a nucleic acid into a host cell are known in the art, and any known method can be used to introduce a nucleic acid (e.g., an expression construct) into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

Contacting cells with a Cas9 targeting complex may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are typically permissive of the subject cleavage and binding methods In some embodiments, a Cas9 protein can be codon optimized. In some cases, a codon optimized Cas9 protein is a variant Cas9 protein. In some cases, a codon optimized Cas9 protein is a chimeric Cas9 protein. Codon optimization is known in the art and entails the mutation of foreign-derived DNA to mimic the codon preferences of the intended host organism or host cell while encoding the same protein. Thus, the codons are changed, but the encoded protein remains unchanged. For example, if the intended target cell was a human cell, a human codon optimized Cas9 (or Cas9 variant) would be a suitable Cas9 protein. As another non-limiting example, if the intended host cell were a mouse cell, than a mouse codon optimized Cas9 (or variant, e.g., enzymatically inactive variant) would be a suitable Cas9 protein. While codon optimization is not required, it is acceptable and may be preferable in certain cases.

In some embodiments, a component of a Cas9 targeting complex (e.g., a targeter-RNA, an activator-RNA, a guide RNA (e.g., a single guide RNA), and/or a Cas9 protein) can be provided as RNA. In such cases, the component of a Cas9 targeting complex can be produced by direct chemical synthesis or may be transcribed in vitro from a DNA (e.g., encoding the component). Methods of synthesizing RNA from a DNA template are well known in the art. In some cases, the component or components will be synthesized in vitro using an RNA polymerase enzyme (e.g., T7 polymerase, T3 polymerase, SP6 polymerase, etc.). Once synthesized, the RNA may be introduced into a cell by any of the well-known techniques for introducing nucleic acids into cells (e.g., microinjection, electroporation, transfection, nucleofection, etc). A component of a Cas9 targeting complex can be produced using any convenient method (e.g., chemical synthesis).

Any of the components of a Cas9 targeting complex may be provided to the cells using any convenient transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008 Efficient gene targeting in Drosophila by direct embryo injection with zinc-finger nucleases. PNAS 105(50):19821-19826. Alternatively, nucleic acids encoding any of the components of a Cas9 targeting complex may be provided on DNA vectors. Many vectors, e.g. plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, etc.

In some embodiments, a targeting complex can be formed (e.g., in vitro) prior to contact with a target DNA (e.g., prior to introduction into a cell). For example, in some cases, a Cas9 protein is combined with a guide RNA (thus forming a ribonucleoprotein (RNP) that can be referred to as a targeting complex), prior to introduction into a cell. Delivery of the targeting complex (the resulting RNP) can be achieved by any convenient method (e.g., nucleofection, direct injection, or any other method of delivering nucleic acid and/or protein to a cell, e.g., as discussed herein).

Vectors may be provided directly to the subject cells. In other words, the cells are contacted with vector(s) comprising the nucleic acid(s) encoding a component(s) of a Cas9 targeting complex such that the vector(s) is/are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising the nucleic acid encoding at least one component of a Cas9 targeting complex. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also introduced by direct micro-injection (e.g., injection of RNA into a zebrafish embryo).

Vectors used for providing the nucleic acids encoding a component(s) of a Cas9 targeting complex to the subject cells will typically comprise suitable promoters for driving the expression, that is, transcriptional activation, of the nucleic acid of interest. In other words, the nucleic acid of interest will be operably linked to a promoter (e.g., a eukaryotic promoter). This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a component of a Cas9 targeting complex may include nucleic acid sequences that encode for selectable markers in the target cells, so as to identify cells that have taken up the vectors.

A subject component of a Cas9 targeting complex (e.g., a targeter-RNA, an activator-RNA, a guide RNA (e.g., a single guide RNA), and/or a Cas9 protein) may be used to contact DNA or may be introduced into cells as RNA. Methods of introducing RNA into cells are known in the art and may include, for example, direct injection, transfection, or any other method used for the introduction of DNA.

A subject Cas9 protein may be provided to cells as a polypeptide. Such a polypeptide may optionally be fused to a polypeptide domain (e.g., to increase solubility of the product, to allow for affinity purification, etc.). The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, MBP domain, His tag, HA tag, FLAG tag, GRPE domain, and the like. The polypeptide may be formulated for improved stability. For example, the peptides may be PEGylated, where the polyethyleneoxy group provides for enhanced lifetime in the blood stream.

Additionally or alternatively, the subject Cas9 protein may be fused to a polypeptide permeant domain to promote uptake by the cell. A number of permeant domains are known in the art and may be used in the non-integrating polypeptides of the present invention, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 268) As another example, the permeant peptide comprises the HIV-1 tat basic region amino acid sequence, which may include, for example, amino acids 49-57 of naturally-occurring tat protein. Other permeant domains include polyarginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A subject Cas9 protein may be produced in vitro or by eukaryotic cells or by prokaryotic cells, and it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are targeter-RNAs, activator-RNAs, guide RNAs, and Cas9 proteins that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc) or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The Cas9 proteins may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The Cas9 proteins may also be isolated and purified in accordance with conventional methods of recombinant synthesis (e.g., using an affinity tag such as a HIS tag, and HA tag, etc.). A lysate may be prepared of the expression host and the lysate purified using HPLC, exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein.

To induce cleavage or any desired modification to a target DNA, or any desired modification to a polypeptide associated with target DNA, the guide RNA and/or the Cas9 protein, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different guide RNAs that are complementary to different sequences within the same or different target DNA), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

Nucleic Acid Modifications

In some embodiments, a subject nucleic acid (e.g., a guide RNA, a PAM-mer, etc.) has one or more modifications, e.g., a base modification, a backbone modification, etc, to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid (e.g., a guide RNA, a PAM-mer, etc.) has one or more nucleotides that are 2'-O-Methyl modified nucleotides. In some embodiments, a subject nucleic acid (e.g., a guide RNA, a PAM-mer, etc.) has one or more 2' Fluoro modified nucleotides. In some embodiments, a subject nucleic acid (e.g., a guide RNA, a PAM-mer, etc.) has one or more LNA bases. In some embodiments, a subject nucleic acid (e.g., a guide RNA, a PAM-mer, etc.) has one or more nucleotides that are linked by a phosphorothioate bond (i.e., the subject nucleic acid has one or more phosphorothioate linkages). In some embodiments, a subject nucleic acid (e.g., a guide RNA, a PAM-mer, etc.) has a 5' cap (e.g., a 7-methylguanylate cap (m7G)). In some embodiments, a subject nucleic acid (e.g., a guide RNA, a PAM-mer, etc.) has a combination of modified nucleotides. For example, a subject nucleic acid (e.g., a guide RNA, a PAM-mer, etc.) can have a 5' cap (e.g., a 7-methylguanylate cap (m7G)) in addition to having one or more nucleotides with other modifications (e.g., a 2'-O-

Methyl nucleotide and/or a 2' Fluoro modified nucleotide and/or a LNA base and/or a phosphorothioate linkage).

In some embodiments, a subject guide RNA has one or more nucleotides that are 2'-O-Methyl modified nucleotides. In some embodiments, a subject guide RNA has one or more 2' Fluoro modified nucleotides. In some embodiments, a subject guide RNA has one or more LNA bases. In some embodiments, a subject guide RNA has one or more nucleotides that are linked by a phosphorothioate bond (i.e., the subject nucleic acid has one or more phosphorothioate linkages). In some embodiments, a subject guide RNA has a 5' cap (e.g., a 7-methylguanylate cap (m7G)). In some embodiments, a subject guide RNA has a combination of modified nucleotides. For example, a subject guide RNA can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target DNA. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($—CH_2—$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638.

The synthesis and preparation of the LNA monomers adenine, cytosine, guanine, 5-methyl-cytosine, thymine and uracil, along with their oligomerization, and nucleic acid recognition properties have been described (e.g., Koshkin et al., Tetrahedron, 1998, 54, 3607-3630). LNAs and preparation thereof are also described in WO 98/39352 and WO 99/14226, as well as U.S. applications 20120165514, 20100216983, 20090041809, 20060117410, 20040014959, 20020094555, and 20020086998.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2$ $CH_2$ $CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278 and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538, an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus of an exogenous polypeptide (e.g., a Cas9 protein). In some embodiments, a PTD is covalently linked to the carboxyl terminus of an exogenous polypeptide (e.g., a Cas9 protein). In some embodiments, a PTD is covalently linked to a nucleic acid (e.g., a guide RNA, a polynucleotide encoding a guide RNA, a polynucleotide encoding a Cas9 protein, etc.). Exemplary PTDs include but are not limited to a minimal undecapeptide protein transduction domain (corresponding to residues 47-57 of HIV-1 TAT comprising YGRKKRRQRRR; SEQ ID NO:264); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008; RRQRRTSKLMKR (SEQ ID NO:265); Transportan GWTLNSAGYLLGKINLKA-LAALAKKIL (SEQ ID NO:266); KALAWEAKLAKA-LAKALAKHLAKALAKALKCEA (SEQ ID NO:267); and RQIKIWFQNRRMKWKK (SEQ ID NO:268. Exemplary PTDs include but are not limited to, YGRKKRRQRRR (SEQ ID NO:264), RKKRRQRRR (SEQ ID NO:269); an arginine homopolymer of from 3 arginine residues to 50 arginine residues; Exemplary PTD domain amino acid sequences include, but are not limited to, any of the following: YGRKKRRQRRR (SEQ ID NO:264); RKKRRQRR (SEQ ID NO:270); YARAAARQARA (SEQ ID NO:271); THRLPRRRRRR (SEQ ID NO:272); and GGRRAR-RRRRR (SEQ ID NO:273). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Additional Examples

Additional targeter-RNAs, activator-RNAs, Cas9 proteins (including variant Cas9 proteins), single guide RNA, etc., and methods of using the same, can be found in the literature (see, for example, Chylinski et al., RNA Biol. 2013 May; 10(5):726-37; Jinek et al., Science. 2012 Aug. 17; 337 (6096):816-21; Ma et al., Biomed Res Int. 2013; 2013: 270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10): 1163-71; Cho et. al., Genetics. 2013 November; 195(3): 1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. al., Nat Methods. 2013 October; 10(10):957-63; Nakayama et. al., Genesis. 2013 Oct. 12. doi: 10.1002/dvg.22720; Ran et. al., Nat Protoc. 2013 November; 8(11):2281-308; Ran et. al., Cell. 2013 Sep. 12; 154(6):1380-9; Upadhyay et. al., G3 (Bethesda). 2013 Oct. 11. doi:pii: g3.113.008847v1. 10.1534/g3.113.008847; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; all of which are hereby incorporated by reference in their entirety).

Kits

The present disclosure provides kits for carrying out a subject method. A subject kit can include a cell cycle blocking agent and one or more of: (i) a single guide RNA, (ii) a DNA polynucleotide encoding a single guide RNA, (iii) a targeter-RNA, (iv) a DNA polynucleotide encoding a targeter-RNA, (v) an activator-RNA, (vi) a DNA polynucleotide encoding an activator-RNA, (vii) a Cas9 protein, and (h) a nucleic acid encoding a Cas9 protein; all of which are described in detail above. In some cases, a kit includes a donor polynucleotide (e.g, encoding a marker protein, e.g., a fluorescent protein such as GFP, RFP, CFP, YFP, and the like). As noted above, the term Cas9 protein encompasses a variant Cas9 protein, a wild type Cas9 protein, a chimeric Cas9 protein, etc.

Any of the above-described kits can further include one or more additional reagents, where such additional reagents can be selected from: a dilution buffer; a reconstitution solution; a wash buffer; a control reagent; a control expression vector or RNA polynucleotide; a reagent for in vitro production of the Cas9 protein from DNA, and the like. In some cases, a subject kit comprises a variant Cas9 protein (or a nucleotide encoding the same) that exhibits reduced nuclease activity relative to wild-type Cas9. Components of a subject kit can be in separate containers; or can be combined in a single container.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

The CRISPR/Cas9 system is a robust genome editing technology that functions in human cells, animals and plants based on the RNA-programmed DNA cleaving activity of the Cas9 enzyme. Homology-directed repair (HDR) of Cas9-induced site-specific double-strand DNA breaks leads to integration of donor DNA sequences at the break site, enabling targeted genome engineering. However, the more prevalent repair pathway, non-homologous end joining (NHEJ), generates small random insertions or deletions (indels) at the site of the original break. To enhance the efficiency of HDR in human cells, we developed a method for delivery of Cas9 and guide RNA combined with cell cycle synchronization. Cas9 RNP-mediated HDR in HEK293T, primary human fibroblasts and human embryonic stem cells was increased by several fold relative to experiments in unsynchronized cells, while cell mortality and off-target effects were minimized. This approach provides a simple and highly effective strategy for enhancing site-specific genome engineering in both transformed and primary cells.

Materials and Methods

Cell Lines and Cell Culture

DMEM media, fetal bovine serum, non-essential amino acid, penicillin-streptomycin, DPBS and 0.05% trypsin were purchased from Life technologies. 293T cells were maintained in DMEM media supplemented with 10% fetal bovine serum, non-essential amino acid and penicillin-streptomycin. Human neonatal Fibroblasts were maintained in 15% fetal bovine serum, non-essential amino acid and penicillin-streptomycin. H9 human embryonic stem cells were maintained on Matrigel in E8 media plus supplement.

Cell Cycle Synchronization

Aphidicolin, hydroxyurea, lovastatin, mimosine, nocodazole and thymidine were purchased from Sigma-Aldrich. The synchronization protocols were modified from the following references (Adams et al., 1967, J. Biol. Chem. 242, 1314-1317; Harper et al., 2007, Methods in Molecular Biology (Clifton, N.J.) 296, 157-166; Jackman et al., 2001, Curr Protoc Cell Biol Chapter 8, Unit8.3; Pauklin et al., 2003, Cell 155, 135-147). It is important to ensure cells are maintained at <70% confluency. HEK293T cells were seeded at $1\times10^6$ cell density in a 10-cm culture dish. Primary neonatal fibroblast cells were seeded at $5\times10^5$ in 10-cm dish. Human ES cells were maintained in 6 well dishes. Aphidicolin and thymidine require two sequential treatments to enrich cells arrested at the entry of S phase. Cells were treated with aphidicolin (2 µg/ml) or thymidine (5 mM) for 17 h, washed with media to remove the drugs, grown for 8 h, and treated with a second dose of drugs for 17 h. Hydroxyurea (2 mM), lovastatin (40 µM), mimosine (200 µM) and nocodazole (200 ng/ml) require only one treatment for 17 h. Two synchronization conditions were tested in the human ES cell experiment. The first condition was a simple nocodazole treatment for 16 h. The second condition was modified from Pauklin et al., 2003, Cell 155, 135-147. The cells were treated with nocodazole for 16 h, washed to remove the drug, and then treated with aphidicolin for 3 h before nucleofection.

Expression and Purification of Cas9

The recombinant S. pyogenes Cas9 used in this study carries at C-terminus an HA tag and two nuclear localization signal peptides which facilitates transport across nuclear membrane. The protein was expressed with a N-terminal hexahistidine tag and maltose binding protein in E. coli Rosetta 2 cells (EMD Millipore) from plasmid pMJ915. The His tag and maltose binding protein were cleaved by TEV protease, and Cas9 was purified by the protocols described in Jinek et al 2012 (Jinek et al., 2012, Science 337, 816-821). Cas9 was stored in 20 mM 2-[4-(2-hydroxyethyl)piperazin-1-yl]ethanesulfonic acid (HEPES) at pH 7.5, 150 mM KCl, 10% glycerol, 1 mM tris(2-chloroethyl) phosphate (TCEP) at −80° C.

In Vitro T7 Transcription of sgRNA

The DNA template encoding for a T7 promoter, a 20-nt target sequence and the sgRNA scaffold was assembled from synthetic oligonucleotides by overlapping PCR. Briefly, for the EMX1 sgRNA template, the PCR reaction contains 20 nM premix of BS16 (5'-TAA TAC GAC TCA CTA TAG GTC ACC TCC AAT GAC TAG GGG TTT AAG AGC TAT GCT GGA AAC AGC ATA GCA AGT TTA AAT AAG G-3')(SEQ ID NO:1392) and BS6 (5'-AAA AAA AGC ACC GAC TCG GTG CCA CTT TTT CAA GTT GAT AAC GGA CTA GCC TTA TTT AAA CTT GCT ATG CTG TTT CCA GC-3') (SEQ ID NO:1393), 1 µM premix of T25 (5'-TAA TAC GAC TCA CTA TAG-3') (SEQ ID NO:1394) and BS7 (5'-AAA AAA AGC ACC GAC TCG GTG C-3') (SEQ ID NO:1395), 200 µM dNTP and Phusion Polymerase (NEB) according to manufacturer's protocol. The thermocycler setting consisted of 30 cycles of 95° C. for 10 sec, 57° C. for 10 sec and 72° C. for 10 sec. The PCR product was extracted once with phenol:chloroform:isoamylalcohol and then once with chloroform, before isopropanol precipitation overnight at −20° C. The DNA pellet was washed three times with 70% ethanol, dried by vacuum and dissolved in DEPC-treated water. The DYRK1 sgRNA template was assembled from T25, BS6, BS7 and BS14 (5'-TAA TAC GAC TCA CTA TAG GTT CCT TAA ATA AGA ACT TTG TTT AAG AGC TAT GCT GGA AAC AGC ATA GCA AGT TTA AAT AAG G-3') (SEQ ID NO:1396).

A 100-µl T7 in vitro transcription reaction consisted of 30 mM Tris-HCl (pH 8), 20 mM MgCl$_2$, 0.01% Triton X-100, 2 mM spermidine, 10 mM fresh dithiothreitol, 5 mM of each ribonucleotide triphosphate, 100 µg/ml T7 Pol and 1 µM DNA template. The reaction was incubated at 37° C. for 4 h, and 5 units of RNase-free DNaseI (Promega) was added to digest the DNA template 37° C. for 1 h. The reaction was quenched with 2×STOP solution (95% deionized formamide, 0.05% bromophenol blue and 20 mM EDTA) at 60° C. for 5 min. The RNA was purified by electrophoresis in 10% polyacrylamide gel containing 6M urea. The RNA band was excised from the gel, grinded up in a 15-ml tube, and eluted with 5 volumes of 300 mM sodium acetate (pH 5) overnight at 4° C. One equivalent of isopropanol was added to precipitate the RNA at −20° C. The RNA pellet was collected by centrifugation, washed three times with 70% ethanol, and dried by vacuum. To refold the sgRNA, the RNA pellet was first dissolved in 20 mM HEPES (pH 7.5), 150 mM KCl, 10% glycerol and 1 mM TCEP. The sgRNA was heated to 70° C. for 5 min and cooled to room temperature. MgCl$_2$ was added to a final concentration of 1 mM. The sgRNA was again heated to 50° C. for 5 min and cooled to room temperature. Nanodrop and adjust concentration to 100 uM using 20 mM HEPES (pH 7.5), 150 mM KCl, 10% glycerol, 1 mM TCEP, 1 mM MgCl$_2$.

PCR Assembly of HDR Template 6 and 7

Double-stranded HDR template 6 and 7 were prepared by PCR amplification. Template 6 was PCR amplified from single-stranded template 5 (5'-TGG CCA GGG AGT GGC CAG AGT CCA GCT TGG GCC CAC GCA GGG GCC TGG CCA GCA GCA AGC AGC ACT CTG CCC TCG TGG GTT TGT GGT TGC GGA TCC AAG CTT TTG GAG GTG ACA TCG ATG TCC TCC CCA TTG GCC TGC TTC GTG GCA ATG CGC CAC CGG TTG ATG TGA TGG GAG CCC TTC TTC TTC TGC TCG-3') (SEQ ID NO:1397) using primer set (forward 5'-CGA GCA GAA GAA GAA GGG CTC CCA TC-3' (SEQ ID NO:1398) and reverse 5'-TGG CCA GGG AGT GGC CAG AGT CC-3') (SEQ ID NO:1399). The PCR reaction was performed using Phusion Polymerase according to manufacturer's protocol (NEB). The thermocycler setting consisted of 30 cycles of 95° C. for 20 sec, 67° C. for 10 sec and 72° C. for 20 sec. The PCR product was extracted once with phenol:chloroform:isoamylalcohol and then once with chloroform, before isopropanol precipitation overnight at −20° C. The DNA pellet was washed three times with 70% ethanol, dried by vacuum and dissolved in water. The concentration was determined by Nanodrop (Thermo Scientific).

Template 7 was assembled from two fragments (A and B) by overlapping PCR. Fragment A was PCR amplified from HEK293T genomic DNA using the primer set (forward 5'-GCT CAG CCT GAG TGT TGA GGC CCC AGT GGC TGC TCT GG-3' (SEQ ID NO:1400) and reverse 5'-GTG GTT GCG GAT CCA AGC TTT TGG AGG TGA CAT CGA TGT CCT CCC CAT TGG C-3') (SEQ ID NO:1401). Fragment B was amplified using the primer set (forward 5'-CAC CTC CAA AAG CTT GGA TCC GCA ACC ACA AAC CCA CGA GGG CAG AGT GCT GCT TGC-3' (SEQ ID NO:1402) and reverse 5'-TGC GGT GGC GGG CGG GCC CGC CCA GGC AGG CAG GC-3') (SEQ ID NO:1403). Both reaction were performed using Kapa Hot start high-fidelity polymerase (Kapa Biosystems) in high GC buffer according to the manufacturer's protocol. The thermocycler setting consisted of one cycle of 95° C. for 5 min, 30 cycles of 98° C. for 20 sec, 67° C. for 10 sec and 72° C. for 20 sec, and one cycle of 72° C. for 1 min.

Cas9 RNP Assembly and Nucleofection

Cas9 RNP was prepared immediately before experiment by incubating with sgRNA at 1:1.2 molar ratio in 20 µM HEPES (pH 7.5), 150 mM KCl, 1 mM MgCl$_2$, 10% glycerol and 1 mM TCEP at 37° C. for 10 min. HDR donor DNA was then added to the RNP mixture. Cells were dissociated by 0.05% trypsin, spun down by centrifugation at 400 g for 3 min, and washed once with DPBS. Nucleofection of HEK293T cells was performed using Lonza SF cell-kits and program CM130 in an Amaxa 96-well Shuttle system; for primary neonatal fibroblast, P3 primary cell-line kit and program CA137. Each nucleofection reaction consisted of approximately 2×10$^5$ cells in 20 µl of nucleofection reagent and mixed with 10 µl of RNP:DNA. After electroporation, 100 µl of DMEM media was added to the well to transfer the cells to tissue culture plates. The cells were incubated at 37° C. for 24 h, the media was removed by aspiration, and 100 µl of Quick Extraction solution (Epicenter) was added to lyse the cells and extract the genomic DNA. The cell lysate was incubated at 65° C. for 20 min and then 95° C. for 20 min, and stored at −20° C. The concentration of genomic DNA was determined by NanoDrop (Thermo Scientific).

PCR Amplification of Target Region

A 640-nt region of EMX1 and DYRK1 loci, containing the target site, were PCR amplified using the following primer sets. For EMX1: forward 5'-GCC ATC CCC TTC TGT GAA TGT TAG AC-3' (SEQ ID NO:1404) and 5'-GGA GAT TGG AGA CAC GGA GAG CAG-3'(SEQ ID NO:1405). For DYRK1: forward 5'-GAG GAG CTG GTC TGT TGG AGA AGT C-3'(SEQ ID NO:1406) and reverse 5'-CCC AAT CCA TAA TCC CAC GTT GCA TG-3'(SEQ ID NO:1407). These primers were designed to avoid amplifying the HDR templates by annealing outside of the homology arms. The PCR reaction was performed using 200 ng of genomic DNA and Kapa Hot start high-fidelity polymerase (Kapa Biosystems) in high GC buffer according to the manufacturer's protocol. The thermocycler setting consisted of one cycle of 95° C. for 5 min, 30 cycles of 98° C. for 20 sec, 62° C. for 15 sec and 72° C. for 1 min, and one cycle of 72° C. for 1 min. The PCR products were analyzed on 2% agarose gel containing SYBR Safe (Life Technologies). The concentration of PCR DNA was quantitated based on the band intensity relative to a DNA standard using the software Image Lab (Bio-Rad). About 200 ng of PCR DNA was used for T7 endonuclease I and HindIII analyses.

Analysis of NHEJ by T7 Endonuclease I Assay

NHEJ efficiency was determined by T7 endonuclease I assay. T7 endonuclease I recognizes and cleaves mismatched heteroduplex DNA which arises from hybridization of wild-type and mutant DNA strands. The hybridization reaction contained 200 ng of PCR DNA in KAPA high GC buffer and 50 mM KCl, and was performed on a thermocycler with the following setting: 95° C., 10 min, 95-85° C. at −2° C./sec, 85° C. for 1 min, 85-75° C. at −2° C./sec, 75° C. for 1 min, 75-65° C. at −2° C./sec, 65° C. for 1 min, 65-55° C. at −2° C./sec, 55° C. for 1 min, 55-45° C. at −2° C./sec, 45° C. for 1 min, 45-35° C. at −2° C./sec, 35° C. for 1 min, 35-25° C. at −2° C./sec, 25° C. for 1 min, and hold at 4° C. Buffer 2 and 5 units of T7 endonuclease I (NEB) were added to digest the re-annealed DNA. After one hour of incubation at 37° C., the reaction was quenched with one volume of gel loading dye (50 mM Tris pH 8.5, 50 mM EDTA, 1% SDS, 50% glycerol and 0.01% bromophenol blue) at 70° C. for 10 min. The product was resolved on 2% agarose gel containing SYBR gold (Life technologies). The DNA band intensity was quantitated using Image Lab. The percentage of NHEJ was calculated using the following equation $(1-(1-(b+c/a+b+c))^{1/2})\times 100$, where "a" is the band intensity of DNA substrate and "b" and "c" are the cleavage products.

Analysis of HDR by HindIII Restriction Digestion

HindIII directly cleaves PCR DNA containing the newly integrated HindIII restriction sequence as the result of successful HDR. The reaction consisted of 200 ng of PCR DNA and 10 units of HindIII High Fidelity in CutSmart Buffer (NEB). After 2 h of incubation at 37° C., the reaction was quenched with one volume of gel loading dye at 70° C. for 10 min. The product was resolved on 2% agarose gel containing SYBR gold (Life technologies). The band intensity was quantitated using Image Lab. The percentage of HDR was calculated using the following equation $(b+c/a+b+c)\times 100$, where "a" is the band intensity of DNA substrate and "b" and "c" are the cleavage products.

Results

Figure 1B:
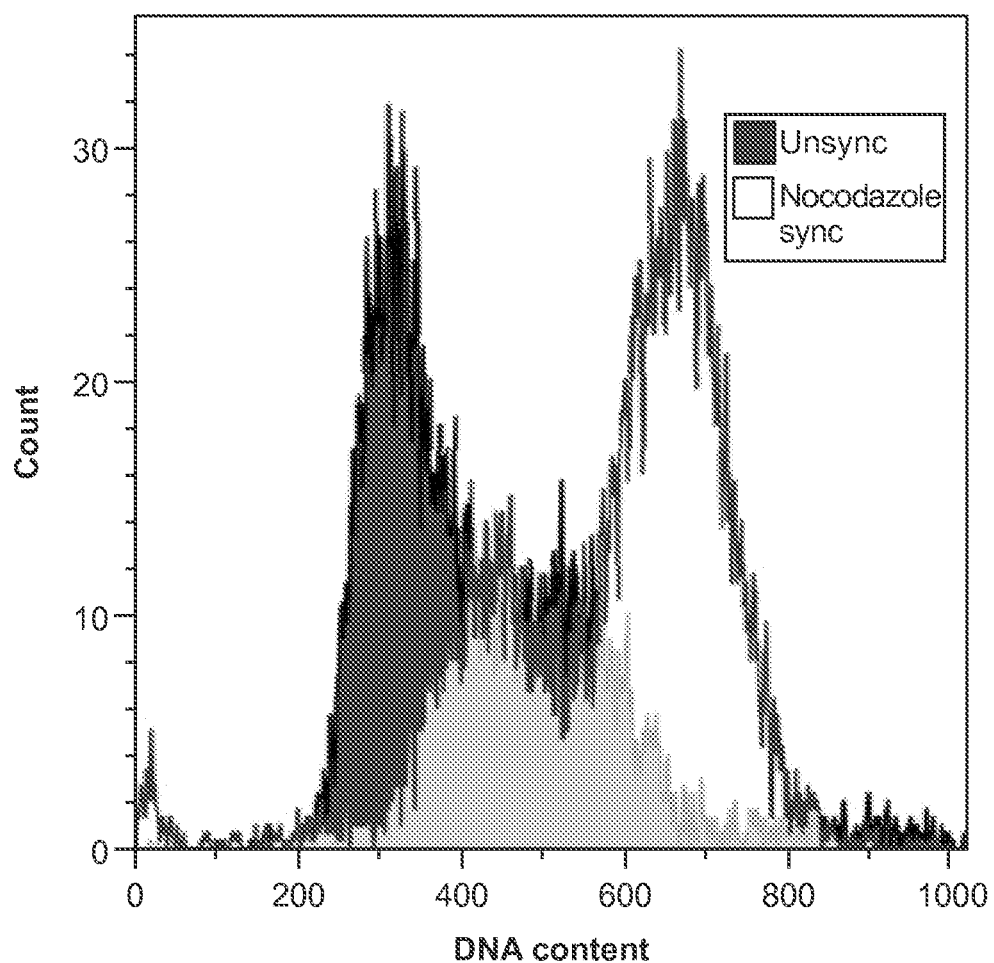

The first objective was to test whether S phase was ideal for HDR in HEK293T cells. The approach was to chemically and reversibly synchronize the cells at G1, S and M phases (FIG. 1A). Lovastatin blocks at early G1 and partially at G2/M phase, by inhibiting HMG-CoA reductase and resulting in the depletion of mevalonate, which is an essential substrate for cholesterol synthesis. Mimosine arrests cells at the G1-S border prior to onset of DNA replication by an unknown mechanism. Aphidicolin reversibly inhibits replicative DNA polymerases. Excess thymidine causes feedback inhibition of deoxycytosine synthesis. Hydroxyurea blocks cells at S phase by decreasing the production of deoxyribonucleotide via inhibition of the enzyme ribonucleotide reductase. Nocodazole inhibits microtubule polymerization which is a signature structural feature as cells enter mitosis, causing arrest at G2/M phase. The drugs effects were confirmed by fluorescence activated cell sorter (FACS) analysis of the cell cycle (FIG. 1B). FACS analysis of the DNA content in the nocodazole-treated cells indicates a two-fold enrichment of the cells arrested at M phase.

Figure 3A:
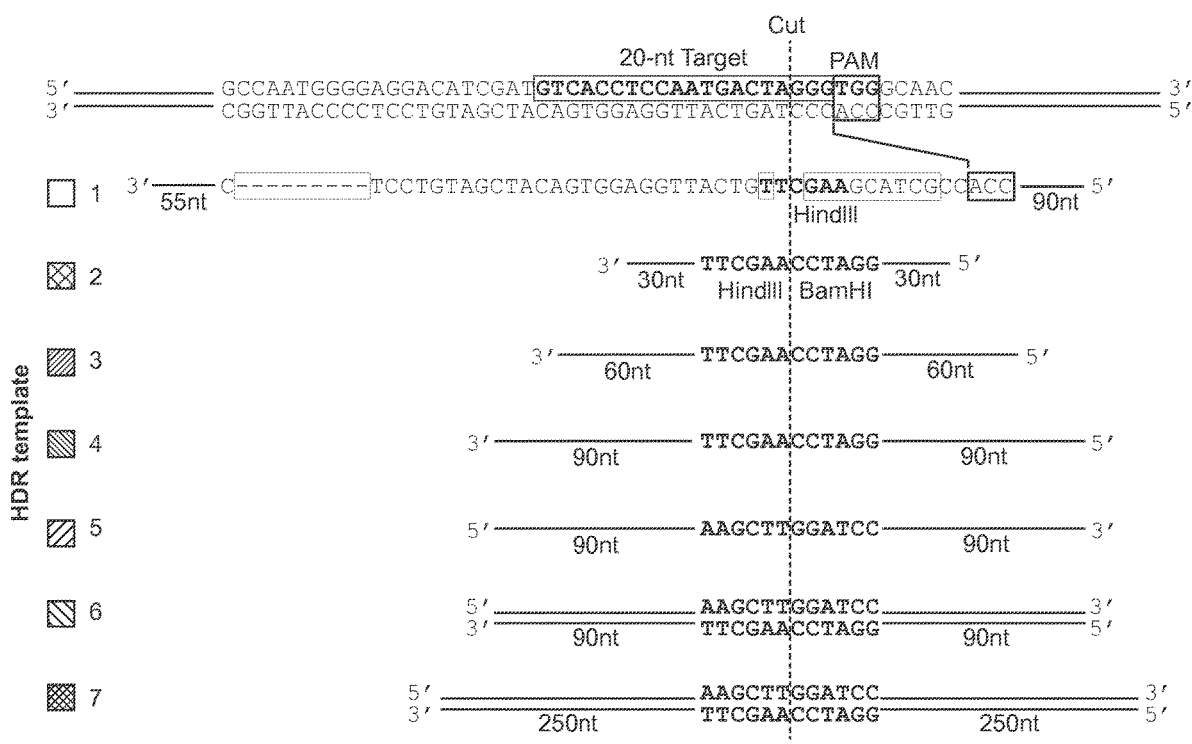
FIG. 3A-3B depict systematic investigation of DNA templates for efficient HDR at the EMX1 locus.

HEK293T cells were synchronized and RNP was prepared by loading Cas9 with a single guide RNA (sgRNA) to target exon 3 of the EMX1 gene (Materials and methods), which encodes the EMX1 transcription factor essential for neural development. Two doses of RNP were co-nucleofected with a donor DNA which was a linear, 183-nt single-strand DNA oligonucleotide (ssODNA) encoding a HindIII restriction site (FIG. 3A template 1). Twenty four hours post nucleofection, the transfected HEK293T cells were collected, genomic DNA extracted, and the target region PCR amplified for NHEJ and HDR analyses. The NHEJ frequency, a functional readout of Cas9 cleavage activity, was measured by T7 endonuclease I assay and calculated using a formula described by Ran et al (Ran et. al., Cell. 2013 Sep. 12; 154(6):1380-9). Using this formula is necessary, because upon re-annealing, one duplex of mutant DNA can produce two duplexes of mutant:wild-type hybrid, doubling the actual NHEJ frequency. The HDR frequency was determined directly by HindIII digestion, which specifically cleaved the newly integrated HindIII sequence, and calculated from the ratio of DNA product to DNA substrate.

Figure 1C:
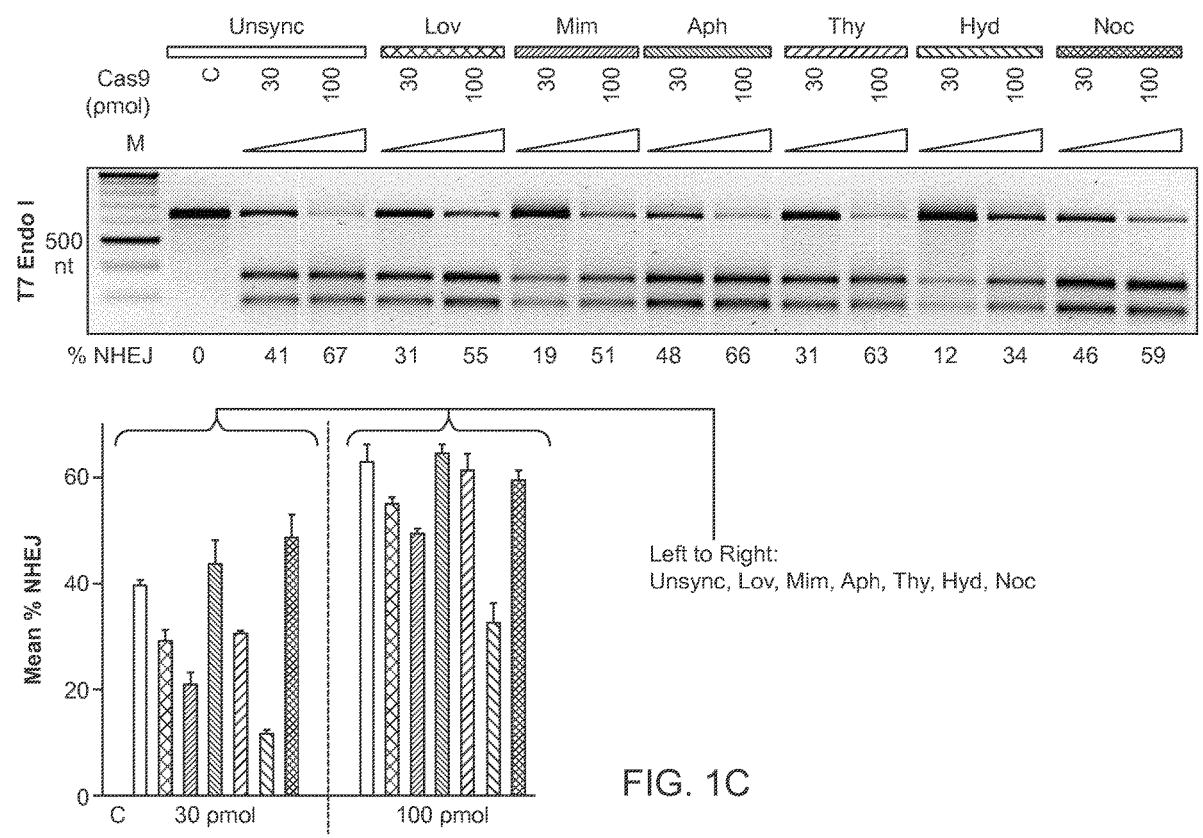
Figure 1D:
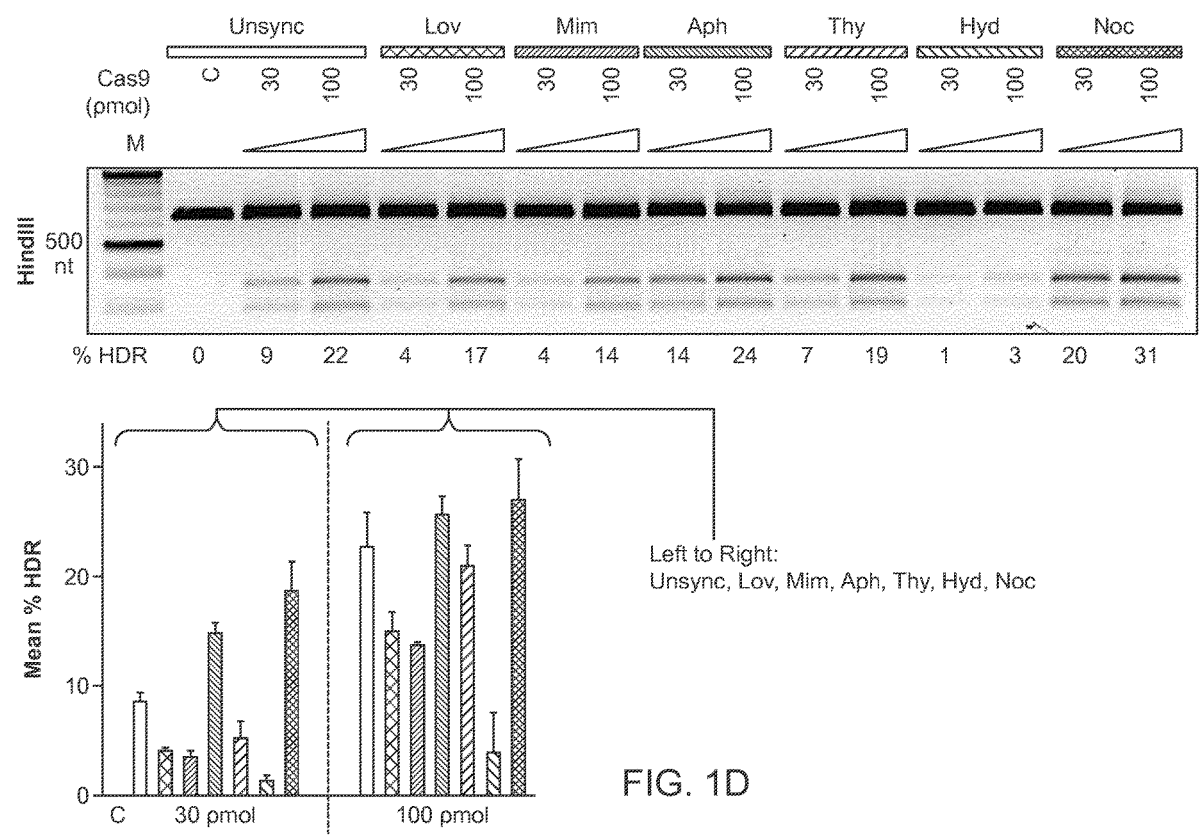

Of the six inhibitors tested, lovastatin, mimosine and hydroxyurea greatly decreased the NHEJ and HDR frequencies as compared to the unsynchronized cells (FIG. 1C and FIG. 1D). Thymidine slightly reduced the NHEJ and HDR frequencies at 30 pmol of Cas9 but not at 100 pmol. Aphidicolin and nocodazole increased the NHEJ frequency slightly at 30 pmol of Cas9; at 100 pmol of Cas9, the detection limit by T7 endonuclease I assay has likely reached the maximum. The HDR frequency was increased by aphidicolin and nocodazole. The enhancement was more evident at 30 pmol of Cas9, 9% in the unsynchronized cells to 15% with aphidicolin and 19% with nocodazole (FIG. 1D). The highest HDR frequency was achieved in the triplicate experiment, which was 31% as shown in the representative gel in FIG. 1D, was obtained by nocodazole synchronization at 100 pmol of Cas9.

FIG. 1A-1D depict the effect of cell cycle synchronization on NHEJ and HDR frequencies in HEK293T cells. (A) Chemical inhibitors were used to arrest cells at specific phases of cell cycle. Lovastatin (Lov) blocks cells in G1 phase by inhibiting cholesterol synthesis. Aphidicolin (Aph), hydroxyurea (Hyd), mimosine (Mim) and thymidine (Thy) disrupt DNA replication, each via a different mechanism, to prevent progression through S phase. Nocodazole (Noc) arrests cells in M phase by inhibiting microtubule polymerization. (B) FACS analysis reveals the DNA content in the cells that are arrested at different phases of cell cycle. Nocodazole treatment results in the accumulation of 4N DNA as compared to the untreated cells, demonstrating a three-fold enrichment of M-phase arrested cells. Screening of cell cycle inhibitors for enhancement in the NHEJ (C) and HDR (D) frequencies in HEK293T cells. For each inhibitor condition (color coded), two doses of Cas9 RNP, 30 and 100 pmol, were transfected with 100 pmol of HDR DNA template 1 (FIG. 3A). Control reaction (labeled as C) contained 100 pmol of Cas9 but no sgRNA. NHEJ frequency was estimated by T7 endonuclease I assay using a formula described in Materials and methods; HDR frequency was measure by HindIII digestion. A representative gel with % NHEJ/HDR is shown for each analysis. The mean % NHEJ/HDR and standard deviation (error bars) were calculated from three experiments.

Figure 2A:
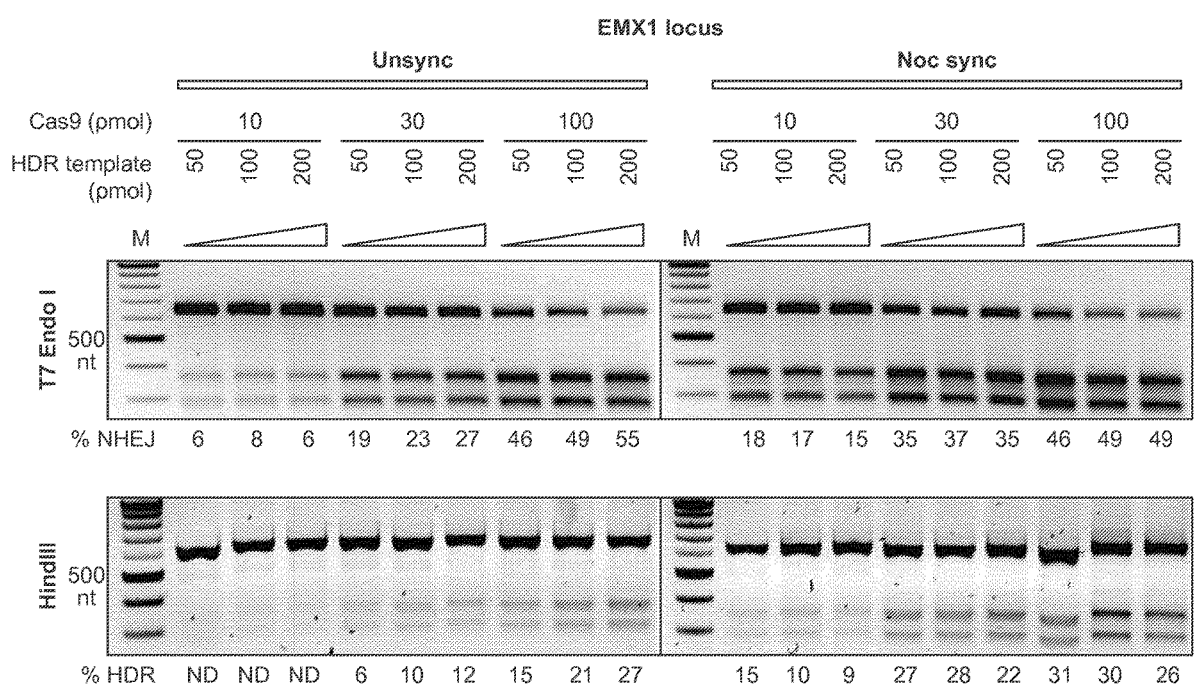
FIG. 2A-2B depict the enhancement of NHEJ and HDR at the EMX1 and DYRK1 loci by nocodazole synchronization.

To determine the NHEJ and HDR frequencies using lower doses of RNP, nocodazole synchronization was used, which gave the greatest HDR enhancement, to systematically determine the dosage effect of Cas9 RNP and HDR template on HDR efficiency. At EMX1 locus, three concentrations of Cas9 RNP (10, 30 and 100 pmol) were tested in combination with three concentrations of HDR template (50, 100 and 200 pmol template 1 in FIG. 3A). As shown in FIG. 2A, the overall frequencies of NHEJ and HDR increased proportionally with Cas9 RNP concentration. The three doses of HDR template yielded comparable HDR frequency, suggesting that 50 pmol was sufficient. In the unsynchronized cells, the NHEJ frequency was 6-8% at 10 pmol, 19-27% at 30 pmol and 46-55% at 100 pmol Cas9 RNP. In the nocodazole-treated cells, the NHEJ frequency was 15-17% at 10 pmol, 35-37% at 30 pmol, 46-49% at 100 pmol Cas9 RNP. Synchronization increased the NHEJ frequency two-fold at 10 pmol and 1.5-fold at 30 pmol Cas9 RNP, but the enhancement diminished at 100 pmol as seen previously. By contrast, the HDR frequency increased dramatically with synchronization, especially at lower doses of Cas9 RNP. Without synchronization, HDR was undetected at 10 pmol Cas9 RNP, while at 30 and 100 pmol Cas9 RNP, the HDR frequencies were 6-12% and 15-27% respectively (FIG. 1A, left panels). With synchronization, HDR efficiency was 9-15% at 10 pmol, 22-28% at 30 pmol and 24-32% at 100 pmol Cas9 RNP (FIG. 1A, right panels). These results demonstrate that controlled-timing of Cas9 RNP delivery into the M-phase synchronized HEK293T cells enhances HDR at this locus.

Figure 2B:
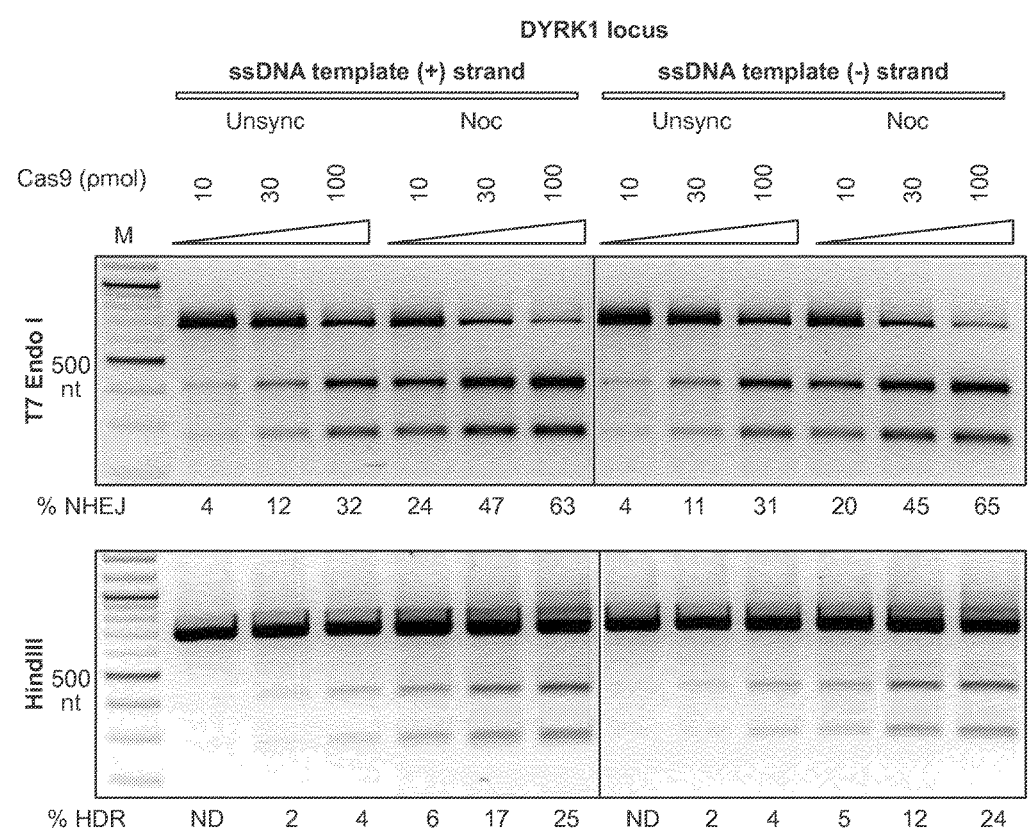

To confirm the observations that were made at the EMX1 locus (above), the DYRK1 gene, which encodes a dual-specificity tyrosine phosphorylation-regulated kinase important for brain development and Downs Syndrome (Anon et al., 2006, Nature 441, 595-600), was targeted. Two, single-stranded HDR templates of different orientations were assayed: one was complementary (+) to the target sequence and the other was non-complementary (−). Both templates yielded comparable levels of HDR, suggesting that the HDR machinery could use either orientation for repair. At this locus, the enhancement of HDR by nocodazole synchronization was more dramatic. Without synchronization, NHEJ and HDR were barely detectable at 10 picomoles (pmol) Cas9 RNP. At 30 and 100 pmol Cas9 RNP, the frequencies increased to 11-12% NHEJ/2% HDR and 31-32% NHEJ/4% HDR respectively (FIG. 2B). By contrast, the synchronized cells yielded 20-24% NHEJ/5-6% HDR at 10 pmol, 45-47% NHEJ/12-17% HDR at 30 pmol and 63-65% NHEJ/24-25% HDR at 100 pmol Cas9 RNP (FIG. 2B). Strikingly, nocodazole synchronization enhanced the NHEJ and HDR frequencies more than two-fold and over six-fold at all doses of Cas9 RNP respectively. Collectively, the results from targeting of EMX1 and DYRK1 loci demonstrate that nocodazole synchronization is highly effective at enhancing both NHEJ and HDR, especially at low doses of Cas9 RNP.

FIG. 2A-2B depict the enhancement of NHEJ and HDR at the EMX1 and DYRK1 loci by nocodazole synchronization. (A) The effect of nocodazole on the NHEJ and HDR frequencies at EMX1 locus. HEK293T cells were synchronized at M phase with 200 ng/ml of nocodazole for 17 h before nucleofection. To determine the optimal dosage, three concentrations of Cas9 RNP were assayed in combination with three doses of HDR template (template 1 in FIG. 3A). The NHEJ frequencies at 10 pmol of Cas9 RNP in the unsynchronized cells were too low and therefore not determined (ND). (B) The effect of nocodazole on the NHEJ and HDR frequencies at DYRK1 locus. The directionality of HDR templates, either in the form of complementary (+) or non-complementary (−) strands was examined. The HDR frequencies at 10 pmol of Cas9 RNP in the unsynchronized cells were also below detection level (ND).

The length of HDR template homology arms required for competent homologous recombination was then examined. Using EMX1 as target, four single-stranded and two double-stranded HDR templates with homology arms ranging from 30 to 250 nt in length were designed (FIG. 3A). The HDR templates contained two restriction sites at the center; a HindIII site to the left of cleavage site and a BamHI to the right. Successful recombination of the HDR templates at the target site integrates these sequences, and mutates the NGG PAM and 6 nt of the Cas9 target sequence, preventing Cas9 from re-targeting the recombined locus. To avoid signal saturation and better distinguish the HDR frequencies of different templates, the concentration of Cas9 RNP was lowered to 30 pmol and the HDR template to 50 pmol. In addition to the unsynchronized and nocodazole synchronized cells, a third condition of HEK293T cells was prepared in which aphidicolin was added immediately after transfection to the growth media to block the cells from entering S phase. We hypothesized this would cause a reduction in HDR frequency due to the inability to enter S phase where HDR pathway is most active.

Figure 3B:
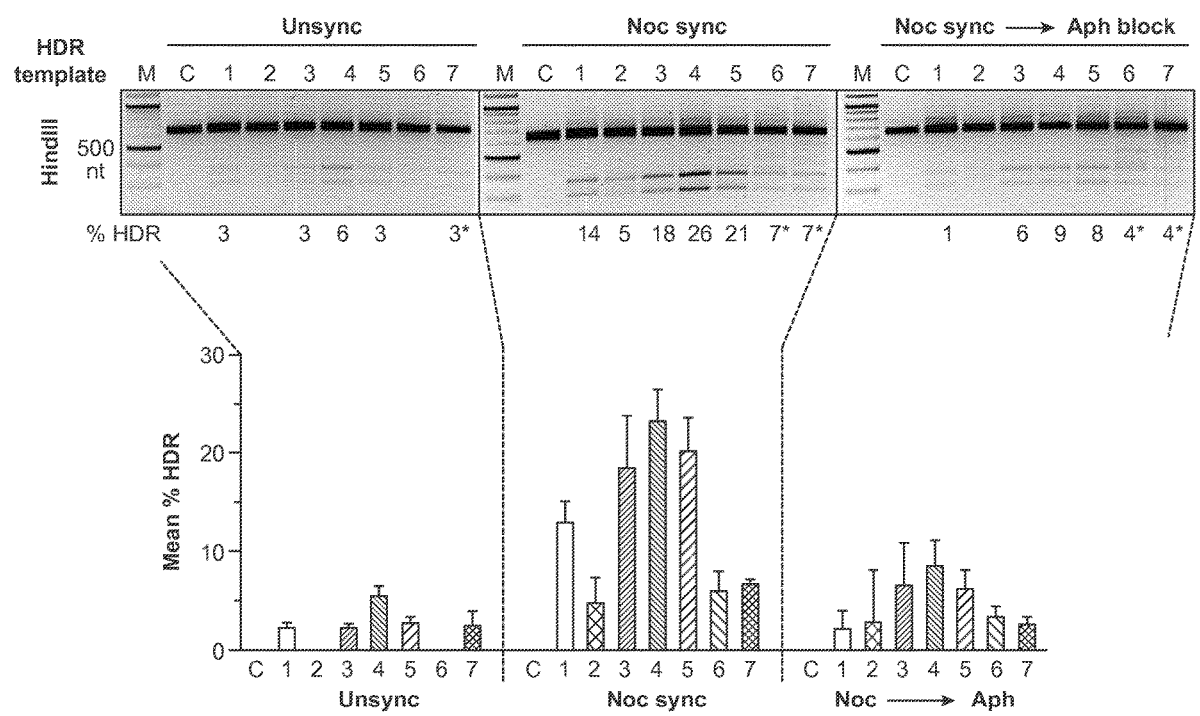

As seen previously, nocodazole synchronization facilitated an overall higher HDR frequency than the unsynchronized cells (FIG. 3B). Also, the aphidicolin block significantly reduced the HDR frequency, demonstrating that the cells need to proceed through S phase, and possibly G2 phase as well, to achieve high HDR. It is important to note that complete elimination of HDR events was not observed; this was likely due to some fraction of cells leaking through the aphidicolin block.

As shown in FIG. 3B, with nocodazole synchronization, a single-stranded oligonucleotide with 30-nt homology arms (template 2) was sufficient for detectable HDR, albeit at low frequency (5%). Extending the length of homology arms to 60 nt (template 3) increased the HDR frequency by four-fold to 19%. Further extension of the homology arms to 90 nt increased the HDR frequency only slightly to 23% and 20% for complementary (template 4) and non-complementary templates (template 5), respectively. Both complementary and non-complementary orientations were similarly effective as seen before. The surge in HDR frequency came from extension of the homology arm from 30 to 60 nt, suggesting that 60 nt could be a crucial length for efficient HDR. Supporting this hypothesis, template 1, which is flanked by 55-nt and 90-nt homology arms, had a lower HDR frequency than template 3 (FIG. 3B). When double-stranded template 6 and 7 were used, unusual banding patterns were observed in both the PCR product and the HindIII digestion (FIG. 3B), hinting the presence of concatemerized HDR template or alternate recombination events. As a result, the band intensity of bona fide HDR products was difficult to quantitate accurately for template 6 and 7. The best estimation in the nocodazole synchronized cells gave 7% HDR for both template 6 and 7, suggesting that double-stranded templates could reduce the HDR efficiency and give rise to non-specific recombination products.

FIG. 3A-3B depict systematic investigation of DNA templates for efficient HDR at the EMX1 locus. (A) Segment of human EMX1 exon 3 shows the 20-nt target sequence (highlighted in blue), the TGG PAM region (in red) and the Cas9 cleavage site at three bases upstream from PAM. Seven HDR templates were tested for HDR efficiency. Template 1 is 183-nt long and contains an 9-nt insertion upstream of the cut site, an 9-nt deletion downstream of the cut site and a single mismatch; these modifications (highlighted in gray) are flanked by 90-nt and 55-nt asymmetrical homology arms at 5' and 3' ends, respectively. Recombination with template 1 allows integration of a HindIII restriction site. Template 2-7 (color coded) contain a HindIII and a BamHI sites that are flanked symmetrically by various lengths of homology arm, ranging from 30 nt to 250 nt.

Template 2-5 are synthetic single-stranded DNA oligonucleotides; whereas, template 6-7 are PCR amplified double-stranded DNA (see Materials and methods). (B) HDR efficiency was tested in three cell conditions: unsynchronized, nocodazole synchronized, and nocodazole synchronized and aphidicolin blocked. Thirty pmol of Cas9 RNP and 50 pmol of HDR template were used in the nucleofection reaction; the control reaction (C) contained no HDR template. Aphidicolin was added into the growth media immediately after nucleofection to 2 µg/ml. The mean % HDR and standard deviation (error bar) was determined by HindIII digestion from three experiments. Representative gels from PCR and HDR analyses are shown for each cell condition. Template 6 and 7 gave unusual banding pattern, making quantitation of DNA bands less accurate (labeled by asterisk).

Figure 4A:
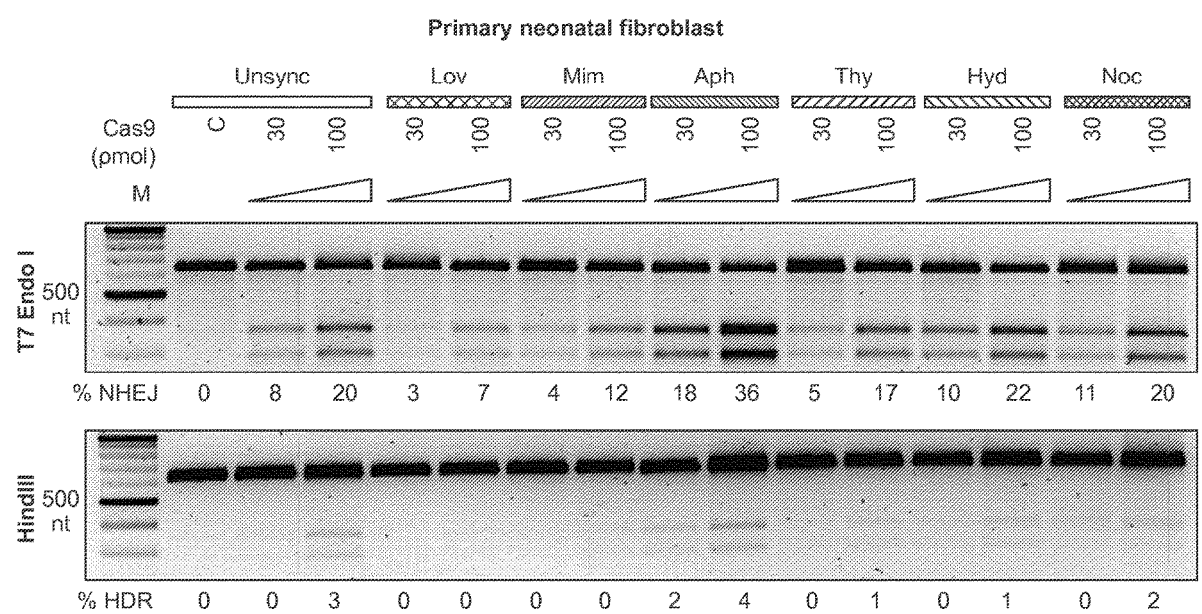
FIG. 4A-4B depict NHEJ and HDR efficiencies at EMX1 locus in human primary neonatal fibroblast and embryonic stem cells.
Figure 4A:
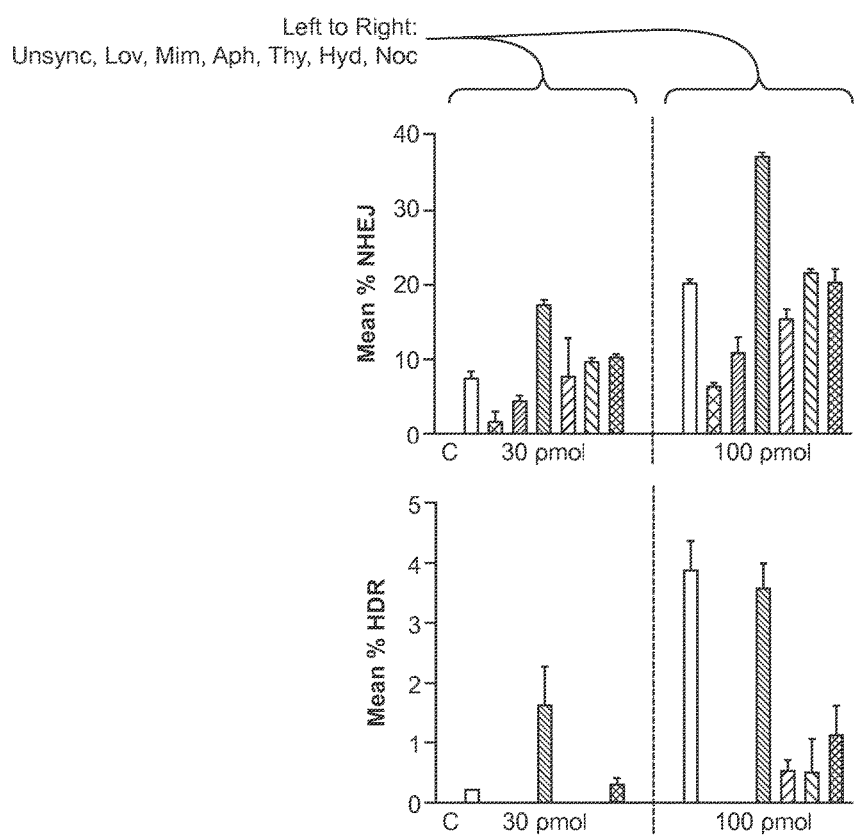

To expand the findings on cell cycle synchronization methods to other cell types, the EMX1 gene was targeted in neoFb (neonatal fibroblasts) and hES (human Embryonic Stem Cells) cells. First, neoFb were subjected to a screening for the optimal cell cycle inhibitor with two doses of Cas9 RNP and template 4, and a different frequency profile was obtained (FIG. 4A). Unlike HEK293T, nocodazole had no effect on neoFb cells. Lovastatin, mimosine and thymidine continued to reduce the NHEJ and HDR frequencies, but hydroxyurea was no longer inhibitory. Aphidicolin was the only tested treatment that enhanced NHEJ and HDR. The NHEJ frequency increased from 8% to 18% at 30 pmol and 20% to 36% at 100 pmol Cas9 RNP. The HDR frequency also increased from barely detectable to 2% at 30 pmol Cas9; at 100 pmol, HDR remained at 4% and no increase was seen (FIG. 4A). The neoFb results demonstrate that different cell types require different synchronization methods.

Figure 4B:
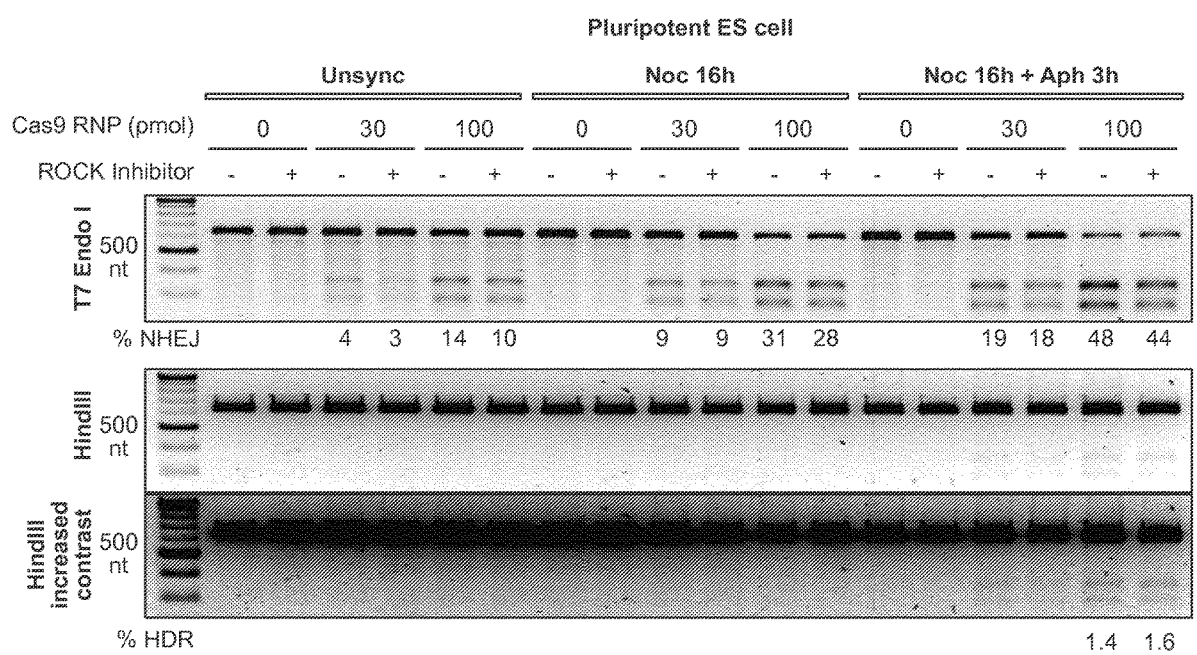

FIG. 4A-4B depict NHEJ and HDR efficiencies at EMX1 locus in human primary neonatal fibroblast and embryonic stem cells. (A) Primary neonatal fibroblast was subjected to the same inhibitor screening as described in the HEK293T experiment. One hundred pmol of Cas9 RNP and 100 pmol of HDR template 4 were used in the nucleofection reaction; the control reaction (C) contained no HDR template. The mean % NHEJ and HDR and standard deviation (error bar) were calculated from three experiments. (B) Three cell conditions were tested in human ES cells: unsynchronized, nocodazole synchronized and nocodazole-aphidicolin sequential synchronized. Thirty or 100 pmol of Cas9 RNP was co-transfected with 100 pmol of HDR template 4, in the presence or absence of ROCK apoptosis inhibitor (10 µM).

Therefore, a different synchronization method was devised for hES cells. Nocodazole synchronization enhanced the NHEJ frequency from 3-4% to 9% at 30 pmol and 10-14% to 28-31% at 100 pmol Cas9 RNP; however, no HDR event was detected (FIG. 1 B). The addition of ROCK apoptosis inhibitor improved the NHEJ frequency slightly. A protocol from Pauklin et al (2013, Cell 155, 135-147) was modified: the cells were treated with nocodazole for 16 h, washed to remove the drug, and then treated with aphidicolin for 3 h before nucleofection. The duration of aphidicolin treatment was shortened, because a substantial drop in cell viability at 10 h was observed. With the new method, ~2% of HDR at 100 pmol Cas9 RNP was detected (FIG. 1B). The contrast of the gel image was increased to show that no HDR was detected in other conditions.

A simple nocodazole treatment can achieve higher HDR efficiency at reduced dosage of Cas9 RNP. Nocodazole blocks cells at M phase when the DNA is fully replicated and the nuclear membrane is broken down. Delivery of Cas9 RNP into a nocodazole synchronized cell may effectively target two cells because they divide upon release. Because the nuclear envelope is broken down, Cas9 RNP may efficiently gain access to the DNA.

Enhanced HDR frequency is useful for generating scarless genetic tools (no introduction of drug selection gene), including epitope-tagged alleles, reporter genes, precise insertion, deletion and point mutations.

REFERENCES

Adams, R. L., and Lindsay, J. G. (1967). Hydroxyurea reversal of inhibition and use as a cell-synchronizing agent. J. Biol. Chem. 242, 1314-1317.

Anon, J. R., Winslow, M. M., Pollen, A., Chang, C.-P., Wu, H., Gao, X., Neilson, J. R., Chen, L., Heit, J. J., Kim, S. K., et al. (2006). NFAT dysregulation by increased dosage of DSCR1 and DYRK1A on chromosome 21. Nature 441, 595-600.

Harper, J. V. (2007). Synchronization of Cell Populations in G1/S and G2/M Phases of the Cell Cycle. Methods in Molecular Biology (Clifton, N.J.) 296, 157-166.

Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nat. Biotechnol. 31, 827-832.

Jackman, J., and O'Connor, P. M. (2001). Methods for synchronizing cells at specific stages of the cell cycle. Curr Protoc Cell Biol Chapter 8, Unit8.3.

Jinek, M., Chylinski, K., Fonfara, I., Hauer, M., Doudna, J. A., and Charpentier, E. (2012). A Programmable Dual-RNA-Guided DNA Endonuclease in Adaptive Bacterial Immunity. Science 337, 816-821.

Kim, S., Kim, D., Cho, S. W., Kim, J., and Kim, J. S. (2014). Highly efficient RNA-guided genome editing in human cells via delivery of purified Cas9 ribonucleoproteins. Genome Research 24, 1012-1019.

Pattanayak, V., Lin, S., Guilinger, J. P., Ma, E., Doudna, J. A., and Liu, D. R. (2013). High-throughput profiling of off-target DNA cleavage reveals RNA-programmed Cas9 nuclease specificity. Nat. Biotechnol. 31, 839-843.

Pauklin, S., and Vallier, L. (2013). The Cell-Cycle State of Stem Cells Determines Cell Fate Propensity. Cell 155, 135-147.

Ran, F. A., Hsu, P. D., Lin, C.-Y., Gootenberg, J. S., Konermann, S., Trevino, A. E., Scott, D. A., Inoue, A., Matoba, S., Zhang, Y., et al. (2013). Double Nicking by RNA-Guided CRISPR Cas9 for Enhanced Genome Editing Specificity. Cell 154, 1380-1389.

Example 2

Figure 6C:
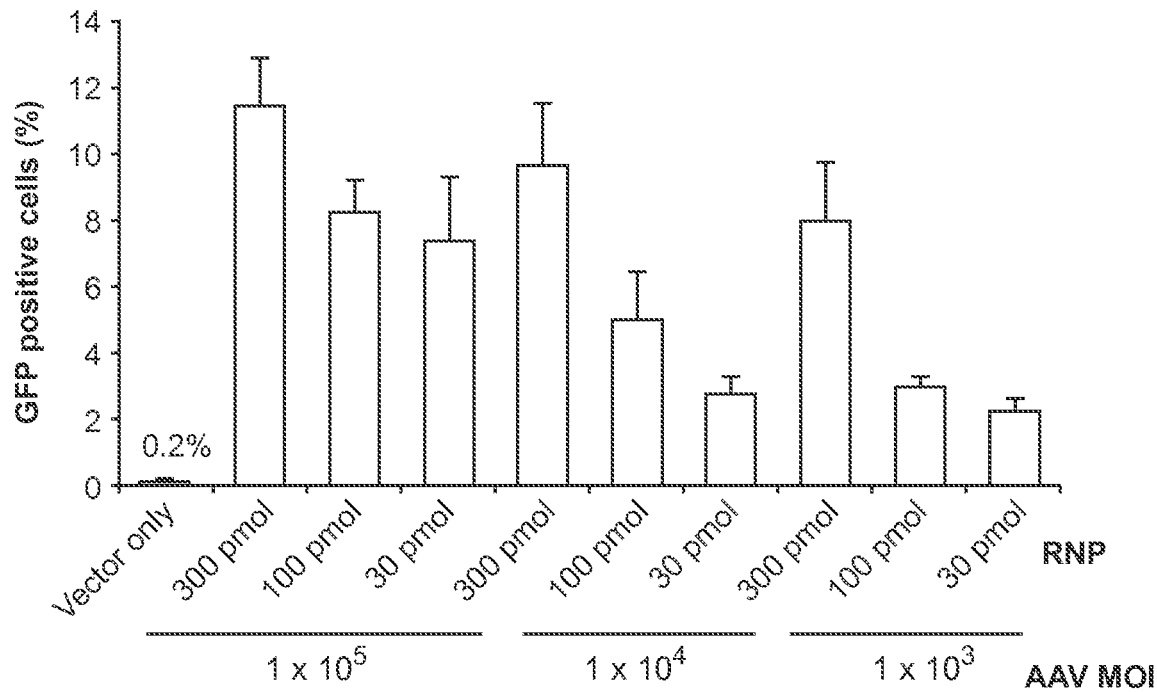
Figure 6D:
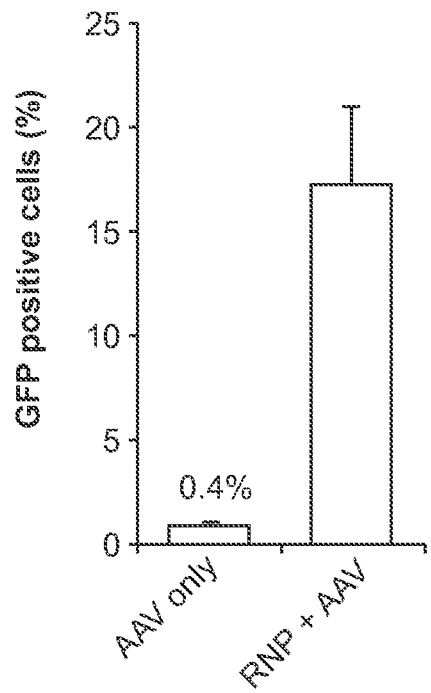
Figure 6E:
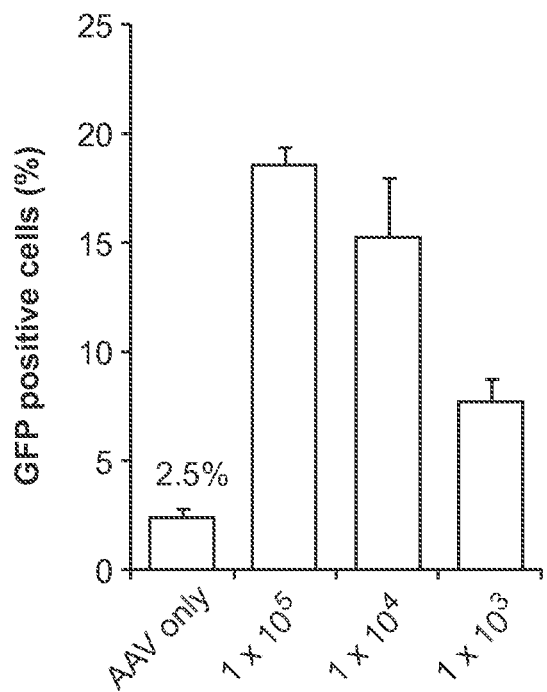
Figure 6F:
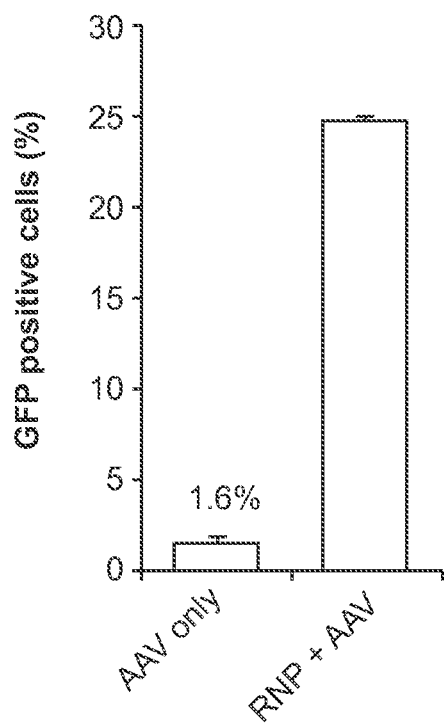

This example demonstrates enhanced gene targeting by cell synchronization and co-delivery of adeno-associated virus (AAV) and Cas9 ribonucleoprotein (RNP). (FIG. 6A) Experimental timeline. (FIG. 6B) Reporter system schematic. A GFP gene (GFPΔ35) was mutated by insertion of a 35 bp fragment and integrated into human embryonic kidney (HEK) 293T and U2OS cells using lentivirus. A targeting vector (t37GFP) containing a 5' truncated GFP coding sequence was packaged into a recombinant AAV vector lacking a promoter. Homologous recombination between donor vector and defective GFPΔ35 led to gene correction and GFP fluorescence. sgRNA target site indicated. (FIG. 6C-FIG. 6F) Percentage of GFP positive (FIG. 6C, FIG. 6D) HEK293T and (FIG. 6E, FIG. 6F) U2OS cells after treatment with 1 µM nocodazole and infection with (FIG. 6C, FIG. 6E) increasing multiplicity of infection (MOI) of AAV or (FIG. 6D, FIG. 6F) 1×10$^5$ MOI of AAV in the (FIG. 6C, FIG. 6E) absence or (FIG. 6D, FIG. 6F) presence of 1 μM Src7 (an inhibitor of nonhomologous end joining). (FIG. 6C) Increasing amounts or (FIG. 6D-FIG. 6F) 300 pmol of RNP was nucleofected into cells 16 h after infection. Error bars indicate standard deviation (n=3).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10570418B2). An electronic copy of the "Sequence Listing" will also be available from the USPTO upon request and payment of the fee set forth in 37 CFR 1.19(b)(3).

What is claimed is:

1. A method of site-specific modification of a target DNA in cells of a population of eukaryotic cells, the method comprising:
   (a) enriching the population of eukaryotic cells for cells in a desired phase of the cell cycle, wherein the desired phase of the cell cycle comprises the M-phase of the cell cycle; and
   (b) contacting the target DNA of cells of the enriched population of cells in vitro with:
      (i) a Cas9 protein or a nucleic acid encoding a Cas9 protein, and
      (ii) a guide RNA comprising: a targeting sequence that hybridizes to a target sequence of the target DNA, and a protein-binding domain that interacts with the Cas9 protein, wherein the method increases site-specific modification of the target DNA by homologous-directed repair (HDR) or non-homologous end joining (NHEJ) by at least 2-fold as compared to the site-specific modification of the target DNA by HDR or NHEJ in the absence of enriching the population of eukaryotic cells for cells in the M-phase of the cell cycle.

2. The method according to claim 1, wherein the desired phase in the cell cycle further comprises the S-phase.

3. The method according to claim 1, wherein the step of enriching comprises at least one of: a cell separation method, and a cell synchronization method.

4. The method according to claim 1, wherein the step of enriching comprises at least one method selected from: mitotic shake-off, countercurrent centrifugal elutriation (CCE), flow cytometry, and contacting the population of eukaryotic cells with a cell cycle blocking composition.

5. The method according to claim 4, wherein the cell cycle blocking composition comprises at least one agent selected from: nocodazole, colchicine, demecolcine, latrunculin A, and latrunculin B.

6. The method according to claim 5, wherein the cell cycle blocking agent is nocodazole.

7. The method according to claim 6, wherein contacting the population of eukaryotic cells with nocodazole increases enrichment of the population of eukaryotic cells in the M-phase of the cell cycle by at least 2-fold.

8. The method according to claim 1, wherein the guide RNA comprises:
   (a) a single guide RNA or a DNA polynucleotide encoding a single guide RNA; or
   (b) a dual guide RNA, wherein the dual guide RNA comprises:
      a targeter-RNA or a DNA polynucleotide encoding a targeter-RNA; and
      an activator-RNA or a DNA polynucleotide encoding an activator-RNA.

9. The method according to claim 1, wherein the Cas9 protein has nuclease activity and the site-specific modification is cleavage of the target DNA.

10. The method according to claim 1, comprising contacting the target DNA with a donor polynucleotide.

* * * * *